US008916366B2

(12) United States Patent
Rao et al.

(10) Patent No.: US 8,916,366 B2
(45) Date of Patent: *Dec. 23, 2014

(54) MULTI-CELLULASE ENZYME COMPOSITIONS FOR HYDROLYSIS OF CELLULOSIC BIOMASS

(75) Inventors: Kripa Rao, San Mateo, CA (US); Ish Dhawan, Foster City, CA (US); Sally Postlethwaite, Redwood City, CA (US); Jie Yang, Foster City, CA (US)

(73) Assignee: Codexis, Inc., Redwood City, CA (US)

( * ) Notice: Subject to any disclaimer, the term of this patent is extended or adjusted under 35 U.S.C. 154(b) by 79 days.

This patent is subject to a terminal disclaimer.

(21) Appl. No.: 13/508,691

(22) PCT Filed: Nov. 18, 2010

(86) PCT No.: PCT/US2010/057163
§ 371 (c)(1),
(2), (4) Date: May 8, 2012

(87) PCT Pub. No.: WO2011/063080
PCT Pub. Date: May 26, 2011

(65) Prior Publication Data
US 2012/0231510 A1    Sep. 13, 2012

Related U.S. Application Data

(60) Provisional application No. 61/263,267, filed on Nov. 20, 2009.

(51) Int. Cl.
| *C12P 7/40* | (2006.01) |
| *C12P 13/04* | (2006.01) |
| *C12P 5/00* | (2006.01) |
| *C12P 7/02* | (2006.01) |
| *C12P 19/02* | (2006.01) |
| *C12N 9/26* | (2006.01) |
| *C12N 9/42* | (2006.01) |
| *C12P 7/10* | (2006.01) |
| *C12P 19/14* | (2006.01) |

(52) U.S. Cl.
CPC .............. *C12P 19/02* (2013.01); *C12N 9/2437* (2013.01); *C12Y 302/01021* (2013.01); *C12N 9/2445* (2013.01); *C12P 7/10* (2013.01); *Y02E 50/16* (2013.01); *C12Y 302/01091* (2013.01); *C12Y 302/01004* (2013.01); *C12P 19/14* (2013.01)
USPC ........... 435/136; 435/106; 435/166; 435/155; 435/105; 435/201; 435/209

(58) Field of Classification Search
None
See application file for complete search history.

(56) References Cited

U.S. PATENT DOCUMENTS

| 6,117,679 | A | 9/2000 | Stemmer |
| 6,376,246 | B1 | 4/2002 | Crameri et al. |
| 6,586,182 | B1 | 7/2003 | Patten et al. |
| 7,923,236 | B2 * | 4/2011 | Gusakov et al. .............. 435/209 |
| 8,088,608 | B2 * | 1/2012 | Yang et al. ..................... 435/183 |
| 8,206,960 | B1 * | 6/2012 | Yang et al. ..................... 435/183 |
| 8,357,523 | B2 * | 1/2013 | Postlethwaite et al. ........ 435/201 |
| 2002/0164730 | A1 | 11/2002 | Ballesteros Perdices et al. |
| 2003/0119018 | A1 | 6/2003 | Omura et al. |
| 2008/0220990 | A1 | 9/2008 | Fox |
| 2009/0312196 | A1 | 12/2009 | Colbeck et al. |
| 2009/0325240 | A1 * | 12/2009 | Daniell ......................... 435/101 |
| 2010/0267089 | A1 * | 10/2010 | Yang et al. ....................... 435/72 |
| 2010/0317059 | A1 * | 12/2010 | Postlethwaite et al. .......... 435/72 |
| 2012/0156754 | A1 * | 6/2012 | Dhawan et al. .............. 435/209 |
| 2012/0178132 | A1 * | 7/2012 | Yang et al. ....................... 435/99 |

FOREIGN PATENT DOCUMENTS

| WO | 2009/108941 A2 | 9/2009 |
| WO | WO 2010120557 A1 * | 10/2010 |
| WO | WO 2010148128 A1 * | 12/2010 |
| WO | 2011/028708 A1 | 3/2011 |
| WO | WO 2011028708 A1 * | 3/2011 |

OTHER PUBLICATIONS

GenBank Accession No. Q82QF4, Nov. 2006, 2 pages.*
GenBank Accession No. Q9F0N9, Nov. 2006, 2 pages.*
GenBank Accession No. AB078006, May 2005, 3 pages.*
Adams, S.P., et al., "Hindered dialkylamino nucleoside phosphite reagents in the synthesis of two DNA 51-mers," J. Am. Chem. Soc., 105:661 (1983).
Altschul, S.F., et al., "Gapped BLAST and PSI-BLAST: a new generation of protein database search programs," Nucleic Acids Res., 25(17):3389-3402 (1997).
Beaucage, S.L., et al., "Deoxynucleoside phosphoamidites—A new class of key intermediates for deoxypolynucleotide synthesis," Tetrahedron Letters, 22(20):1859-62 (1981).
Breves, R., et al., "Genes encoding two different beta-glucosidases of *Thermoanaerobacter brockii* are clustered in a common operon," Appl. Environ. Microbiol,. 63(10):3902-3910 (1997).
Caruthers, M.H., et al., "Chemical Synthesis and Biological Studies on Mutated Gene-control Regions," Cold Spring Harbor Symp. Quant. Biol., 47:411-418 (1982).
Chen, R., et al., "Kinetic and Modeling Investigationon Two-Stage Reverse-Flow Reactor as Applied to Dilute-Acid Pretreatment of Agricultural Residues," Appl. Biochem.Biotechnol., 57/58: 133-146 (1996).
Dayhoff, M.O., et al. , "A model of evolutionary change in proteins" in "Atlas of Protein Sequence and Structure," vol. 5, Suppl. 3 , pp. 345-352, Natl. Biomed. Res. Round., Washington, D.C. (1978).
Duff, S.J.B., et al., "Bioconversion of Forest Products Industry Waste Cellulosics to Fuel Ethanol: A Review," Biores. Technol., 55: 1-33 (1996).

(Continued)

Primary Examiner — David J Steadman
(74) Attorney, Agent, or Firm — Codexis, Inc.

(57) ABSTRACT

The invention relates to a multi-cellulase enzyme composition for the enzymatic hydrolysis of cellulosic biomass said composition comprising a cellobiohydrolase (CBH) enzyme, an endoglucanase (EG) enzyme and a β-glucosidase (BG) enzyme.

17 Claims, 7 Drawing Sheets

(56) References Cited

OTHER PUBLICATIONS

Esteghlalian, A., et al., "Modeling and Optimization of the Dilute-Sulfuric-Acid Pretreatment of Corn Stover,Poplar and Switchgrass," Bioresour. Technol., 59:129-136 (1997).

Faure, D., et al., "The celA Gene, Encoding a Glycosyl Hydrolase Family 3 beta-Glucosidase in *Azospirillum irakense*, Is Required for Optimal Growth on Cellobiosides," Appl. Environ. Microbio, 67(5):2380-2383 (2001).

Gollapalli, L.E., et al., "Predicting digestibility of ammonia fiber explosion (AFEX)—treated rice straw," Appl. Biochem. Biotechnol., 98-100:23-35 (2002).

Henikoff, S., et al. "Amino acid substitution matrices from protein blocks," Proc. Natl. Acad. Sci. USA, 89:10915-10919 (1992).

Knappert, D., et al., "Partial Acid Hydrolysis of Cellulosic Materials as a Pretreatment for Enzymatic Hydrolysis," Biotechnol. Bioeng., 22:1449-1463 (1980).

Kumar, A., et al., "Optimizing the use of cellulase enzymes in finishing cellulosic fabrics," Textile Chemist and Colorist, 29:37-4 (1997).

Ladisch, M.R., et al., "Process considerations in the enzymatic hydrolysis of biomass," Enzyme Microb. Technol., 5:82 (1983).

Matthes, H.W.D., et al., "Simultaneous rapid chemical synthesis of over one hundred oligonucleotides on a microscale," EMBO J., 3(4):801-05 (1984).

Sassner, P., et al., "Bioethanol production based on simultaneous saccharification and fermentation of steam-pretreated Salix at high dry-matter content," Enzyme Microb. Technol., 39:756-762 (2006).

Schell, D.J., et al., "Dilute-Sulfuric Acid Pretreatment of Corn Stover in Pilot-Scale Reactor," Appl. Biochem. Biotechnol., 105-108:69-85 [2003].

Teymouri, F., et al., "Optimization of the ammonia fiber explosion (AFEX) treatment parameters for enzymatic hydrolysis of corn stover," Biores. Technol., 96:2014-2018 (2005).

Torget, R., et al., "Dilute-Acid Pretreatment of Corn Residues and Short-Rotation Woody Crops," Appl. Biochem. Biotechnol., 28/29:75-86 (1991).

Swiss-Prot Accession No. Q9F0N9, created Nov. 28, 2006 online, retrieved Jan. 11, 2011from http://www.ncbi.nlm.nih.gov/protein/75465191.

Genpept Accession No. AAA34210, "cellobiohydrolase II [*Hypocrea jecorina*]," retrieved on May 17, 2012 from www.ncbi.nlm.nih.gov/protein/AAA34210.

Genpept Accession No. AAA34212, "endoglucanase I precursor [*Hypocrea jecorina*]," retrieved on May 17, 2012 from www.ncbi.nlm.nih.gov/protein/AAA34212.

Genpept Accession No. AAA34213, "endoglucanase III [*Hypocrea jecorina*]," retrieved on May 17, 2012 from www.ncbi.nlm.nih.gov/protein/AAA34213.

Genpept Accession No. CAH10320, "unnamed protein product [*Hypocrea jecorina*]," retrieved on May 17, 2012 from www.ncbi.nlm.nih.gov/protein/CAH10320.

\* cited by examiner

FIG. 1A
CBH polynucleotide sequence (SEQ ID NO:1)

```
ATGGGGCCTGCTGCACCTACTGCACGTGTGGATAATCCTTATGTAGGCGCGACAATGTACGT
AAATCCAGAATGGTCAGCTCTTGCTGCTTCGGAACCAGGTGGTGATCGTGTTGCAGATCAAC
CTACGGCTGTTTGGTTAGATCGTATTGCAACTATTGAAGGTGTTGATGGAAAAATGGGATTA
CGAGAACATCTTGATGAAGCGTTACAACAAAAGGAAGCGGAGAACTTGTGGTACAGTTAGT
AATTTATGATTTACCTGGTCGTGATTGCGCGGCTCTTGCTAGTAATGGTGAATTAGGTCCTG
ATGAATTAGATCGATATAAAGCGAATATATTGATCCGATTGCAGACATTTTATCGGATTCC
AAATATGAAGGACTTCGTATTGTTACGGTTATTGAACCAGACAGCTTACCTAATTTAGTAAC
AAACGCAGGTGGTACAGATACAACGACAGAAGCATGTACTACTATGAAAGCAAACGGTAATT
ATGAAAAGGGGTATCGTATGCGCTTTCTAAATTAGGTGCAATTCCGAACGTATACAACTAT
ATTGATGCTGCTCATCATGGATGGTTAGGATGGGACACAAATTTTGGGCCATCCGTACAGGA
ATTTTATAAAGTGGCAACATCAAATGGCGCATCCGTTGATGATGTGGCGGGATTTGCAGTCA
ATACAGCTAATTATTCAGCAACTGTAGAACCTTATTTTACGGTTTCAGATACGGTGAATGGG
CAGACGGTACGTCAATCTAAATGGGTTGACTGGAATCAATACGTAGATGAACAAAGTTATGC
GCAGGCTTTACGAAACGAAGCTGTCGCCGCTGGATTTAATAGCGATATTGGTGTGATTATTG
ATACATCCCGAAATGGATGGGGTGGTCCAGATCGCCCTTCAGGGCCTGGCCCTCAAACTTCC
GTAGATGCTTATGTAGATGGATCACGAATTGATCGTCGCGTTCATGTAGGAAATTGGTGTAA
TCAGTCTGGAGCAGGCTTAGGTGAAAGACCAACAGCAGCACCAGCTAGCGGGATTGATGCAT
ATACATGGATTAAACCGCCGGGCGAATCTGATGGAAATTCAGCTCCGGTTGATAATGACGAA
GGAAAAGGATTTGACCGTATGTGTGATCCTAGCTACCAGGGAAACGCTCGCAATGGCTACAA
TCCTTCAGGAGCGTTACCTGATGCACCATTAAGTGGACAATGGTTTTCGGCACAATTTCGTG
AATTAATGCAAATGCATATCCTCCATTATCTTGA
```

FIG. 1B
CBH mature protein sequence (SEQ ID NO:2)

```
MGPAAPTARVDNPYVGATMYVNPEWSALAASEPGGDRVADQPTAVWLDRIATIEGVDGKMGL
REHLDEALQQKGSGELVVQLVIYDLPGRDCAALASNGELGPDELDRYKSEYIDPIADILSDS
KYEGLRIVTVIEPDSLPNLVTNAGGTDTTTEACTTMKANGNYEKGVSYALSKLGAIPNVYNY
IDAAHHGWLGWDTNFGPSVQEFYKVATSNGASVDDVAGFAVNTANYSATVEPYFTVSDTVNG
QTVRQSKWVDWNQYVDEQSYAQALRNEAVAAGFNSDIGVIIDTSRNGWGGPDRPSGPGPQTS
VDAYVDGSRIDRRVHVGNWCNQSGAGLGERPTAAPASGIDAYTWIKPPGESDGNSAPVDNDE
GKGFDRMCDPSYQGNARNGYNPSGALPDAPLSGQWFSAQFRELMQNAYPPLS
```

FIG. 2A

EG-1 polynucleotide sequence (SEQ ID NO:3)

```
GATACTAGTATGGATACTTCTATTTGTGAACCATTTGGATCTACTACAATCCAAGGACGCTA
TGTAGTACAGAATAATCGTTGGGGCACAAGTGAACCGCAATGTATAACAGCAACCGATTCAG
GATTCCGCATTACCCAAGCGGATGGTTCTGTACCAACGAATGGTCCGCCTAAATCTTATCCA
AGTGTCTATAACGGATGTCATTATACAAATTGCTCTCCTGGGACGCCGCTTCCAGCCCAATT
ATCAACAGTTTCATCTGCTCCAACATCTATTAGTTATTCTTACGTGTCAAATGCCATGTATG
ATGCCGCGTACGACATTTGGTTAGATCCAACACCGCGCACAGATGGTGTAAATCGAACAGAA
ATCATGGTGTGGTTTAATAAAGTAGGCAGCGTGCAGCCAGTAGGATCTCAAGTAGGTACGGC
TACGGTGGCAGGCCGACAATGGCAGGTTTGGTCAGGAAATAACGGATCTAATGATGTGCTTA
GTTTCGTAGCTCCAAGTGCCATTACTTCATGGTCTTTTGATGTAATGGACTTTGTTCGTCAA
GCCGTTAGTCGCGGATTAGCTCAACCGTCTTGGTATTTGACATCTGTCCAAGCTGGATTTGA
ACCGTGGCAGAATGGCGCTGGACTAGCAGTAACTTCTTTTTCGTCTACGGTAAACACTGGAG
GCGGCAATCCAGGAGATCCGGGATCTCCTACTGCTTGCAAAGTTGCTTATGCAACGAATGTT
TGGCAAGGTGGATTTACGGCTGACGTAACTGTAACGAATACAGGGTCCTCACCTGTCAATGG
ATGGAAACTTGCTTTTACGTTACCAGCAGGCCAACAAATTACTTCGTCTTGGTCAGCAGGAG
TATCTCCGTCATCTGGAGCAGTGACAGCTTCTAGCCTTGCATACAATGCACAAATTGCAACC
GGGGGACGTGTATCATTTGGATTTCAAGGTAGTTATTCTGGCACATTTGCAGCACCTGCAGG
TTTTTCTTTAAATGGGGCTGCTTGCACAACGGCATGA
```

FIG. 2B

EG-1 mature protein sequence (SEQ ID NO:4)

```
DTSICEPFGSTTIQGRYVVQNNRWGTSEPQCITATDSGFRITQADGSVPTNGPPKSYPSVYN
GCHYTNCSPGTPLPAQLSTVSSAPTSISYSYVSNAMYDAAYDIWLDPTPRTDGVNRTEIMVW
FNKVGSVQPVGSQVGTATVAGRQWQVWSGNNGSNDVLSFVAPSAITSWSFDVMDFVRQAVSR
GLAQPSWYLTSVQAGFEPWQNGAGLAVTSFSSTVNT
```

FIG. 3A

EG-2 polynucleotide sequence (SEQ ID NO:5)

```
GATACTAGTATGGATACTTCTATTTGTGAACCATTTGGATGGACTGTGATCCAAGGACGCTA
TGTAGTACAGAATAATCGTTGGGGCACAAGTGAACCGCAATGTATAACAGCAACCGATTCAG
GATTCCGCATTACCCGCGCGGATGGTTCTAAACCAACGAATGGTCCGCCTAAATCTTATCCA
AGTGTCTATAACGGATGTCATTATACAATTTGCTCTCCTGGGACGCCGCTTCCAGCCCAAAT
TTCAAAAATTTCATCTGCTCCAACATCTATTAGTTATTCTTACGTGTCAAATGCCGTGTATG
ATGCCGCGTACGACATTTGGTTAGATCCAACACCGCGCACAGATGGTGTAAATCGAACAGAA
ATCATGGTGTGGTTTAATAAAGTAGGCAGCGTGCAGCCAGTAGGATCTCAAGTAGGTACGGC
TACGGTGGCAGGCCGACAATGGCAGGTTTGGATGGGAAATAACGGATCTAATGATGTGCTTA
GTTTCGTAGCTCCAAGTGCCATTACTTCATGGTCTTTTGATGTAATGGACTTTGTTCGTCAA
GCCGTTCAGCGCGGATTAGCTCAACCGTCTTGGTATTTGACATCTGTCCAAGCTGGATTTGA
ACCGTGGGAAAATGGCGCTGGACTAGCAGTAACTTCTTTTTCGTCTACGGTAAACACTGGAG
GCGGCAATCCAGGAGATCCGGGATCTCCTACTGCTTGCAAAGTTGCTTATGCAACGAATGTT
TGGCAAGGTGGATTTACGGCTGACGTAACTGTAACGAATACAGGGTCCTCACCTGTCAATGG
ATGGAAACTTGCTTTTACGTTACCAGCAGGCCAACAAATTACTTCGTCTTGGTCAGCAGGAG
TATCTCCGTCATCTGGAGCAGTGACAGCTTCTAGCCTTGCATACAATGCACAAATTGCAACC
GGGGGACGTGTATCATTTGGATTTCAAGGTAGTTATTCTGGCACATTTGCAGCACCTGCAGG
TTTTTCTTTAAATGGGGCTGCTTGCACAACGGCATGA
```

FIG. 3B:

EG-2 mature protein (SEQ ID NO:6)

```
DTSICEPFGWTVIQGRYVVQNNRWGTSEPQCITATDSGFRITRADGSKPTNGPPKSYPSVYN
GCHYTICSPGTPLPAQISKISSAPTSISYSYVSNAVYDAAYDIWLDPTPRTDGVNRTEIMVW
FNKVGSVQPVGSQVGTATVAGRQWQVWMGNNGSNDVLSFVAPSAITSWSFDVMDFVRQAVQR
GLAQPSWYLTSVQAGFEPWENGAGLAVTSFSSTVNT
```

FIG. 4A
BG-1 polynucleotide sequence (SEQ ID NO:7)

AGTGCGGCAATCGCACAGGAAGGAGCAGCTCCGGCCGCTATGTTACATCCAGAGAAATGGCC
TCGACCTGCGACACAACGACTTATTGACCCGGCAGTTGAAAAAAGAGTTGATGCTCTGTTAA
AACAGTTATCTGTTGAAGAAAAGTAGGGCAAGTTATACAGGGTGATATTGGGACAATTACA
CCAGAAGACCTGCGCAAATATCCACTAGGTTCTATTTTAGCCGGAGGAGATAGCGGCCCGAA
TGGAGATGATCGTGCTCCTCCAAAGGAGTGGCTTGATCTAGCTGATGCTTTTTACCGTGTAA
GTTTAGAAAAACGGCCAGGCCATACCCCGATACCAGTGCTTTTTGGCATTGATGCAGTTCAT
GGACATGGCAATATCGGGTCTGCGACAATTTTCCCTCACAATATTGCACTTGGAATGACCCG
TGATCCAGAACTTCTACGAAGAATTGGTGAGGTAACAGCTGAAGAAATGGCTGCCACGGGAA
TTGATTGGACATTTGCGCCTGCACTGTCTGTTGTGAGAGATGATCGATGGGGACGAACGTAT
GAAGGCTTCTCAGAAGATCCAGAAATTGTAGCTTCTTATTCAGCAGCAATTGTGGAAGGCGT
ACAGGGTAAATATGGTTCTAAGGATTTTATGGCGCCGGGTCGCGCGGTAGCGTGCGCAAAGC
ACTTCTTAGCTGATGGTGGAACAGATCAAGGACGCGATCAGGGAGATGCACGCATTTCAGAA
GACGAACTAATTCGCATTCATAATGCTGGATACCCTCCTGCGATTGACGCAGGAGTGCTGAC
AGTAATGGCTTCTTTTTCATCCTGGCAGGGGATTAAACACCATGGCCATAAACAACTTTTAA
CAGATGTATTAAAAGGACAAATGGGGTTTAATGGATTTATTGTGGGGATTGGAATGCTCAT
GACCAAGTACCGGGCTGTACTAAATTTAATTGTCCAACATCTCTTATTGCGGGTTTAGATAT
GTATATGGCCGCCGATTCCTGGAAGCAGCTGTACGAAAACACCTTAGCACAAGTGAAAGATG
GTACTATTCCTATGGCACGTCTAGATGATGCCGTAAGACGAATCTTGCGAGTCAAGGTGTTG
GCTGGCTTATTCGAGAAACCTGCGCCAAAAGATCGTCCGGGGTTACCAGGCCTTGAAACACT
AGGATCACCTGAACATAGAGCCGTAGGCCGTGAAGCTGTTCGAAAAAGCCTAGTTCTTCTTA
AAAATGATAAAGGTACCCTTCCACTGTCACCAAAGGCTAGAGTATTAGTTGCAGGTGACGGA
GCAGATAATATTGGCAAACAGTCGGGGGGCTGGACGATTAGTTGGCAAGGAACTGGAAACCG
TAACGATGAATTTCCGGGTGCTACATCCATTTAGGTGGGATTCGAGACGCTGTAGCTGATG
CAGGAGGGTCCGTAGAATTTGATGTAGCGGGTCAGTATAAAACAAAACCTGATGTAGCTATT
GTTGTTTTTGGCGAAGAACCTTATGCTGAGTTTCGTGGAGATGTGGAGACACTGGAATATCA
ACCAGATCAAAAACAAGATCTTACCCTACTCAAGAAACTGAAAGATCAGGGAATACCTGTTG
TTGCTGTTTTCCTTTCTGGACGACCGATGTGGGTTAATCCTGAACTTAATGCCAGCGATGCT
TTCGTTGCAGCATGGCTTCCTGGCACAGAAGGTGGCGGTGTGGCGGATGTATTGTTTACAGA
CAAAGCGGGAAAAGTACAACATGATTTTGCAGGAAAATTGTCATATAGTTGGCCGCGTACGG
CAGCCCAGACAACAGTTAACCGTGGTGATGCAGATTATAATCCGTTATTTGCGTATGGTTAC
GGTTTAACGTACAAAGATAAATCGAAAGTGGGCACTCTACCTGAAGAAAGTGGAGTACCGGC
TGAAGCGCGACAGAATTGA

FIG. 4B
BG-1 mature protein sequence (SEQ ID NO:8)

```
SAAIAQEGAAPAAMLHPEKWPRPATQRLIDPAVEKRVDALLKQLSVEEKVGQVIQGDIGTIT
PEDLRKYPLGSILAGGDSGPNGDDRAPPKEWLDLADAFYRVSLEKRPGHTPIPVLFGIDAVH
GHGNIGSATIFPHNIALGMTRDPELLRRIGEVTAEEMAATGIDWTFAPALSVVRDDRWGRTY
EGFSEDPEIVASYSAAIVEGVQGKYGSKDFMAPGRAVACAKHFLADGGTDQGRDQGDARISE
DELIRIHNAGYPPAIDAGVLTVMASFSSWQGIKHHGHKQLLTDVLKGQMGFNGFIVGDWNAH
DQVPGCTKFNCPTSLIAGLDMYMAADSWKQLYENTLAQVKDGTIPMARLDDAVRRILRVKVL
AGLFEKPAPKDRPGLPGLETLGSPEHRAVGREAVRKSLVLLKNDKGTLPLSPKARVLVAGDG
ADNIGKQSGGWTISWQGTGNRNDEFPGATSILGGIRDAVADAGGSVEFDVAGQYKTKPDVAI
VVFGEEPYAEFRGDVETLEYQPDQKQDLTLLKKLKDQGIPVVAVFLSGRPMWVNPELNASDA
FVAAWLPGTEGGGVADVLFTDKAGKVQHDFAGKLSYSWPRTAAQTTVNRGDADYNPLFAYGY
GLTYKDKSKVGTLPEESGVPAEARQN
```

FIG. 5A
BG-2 polynucleotide sequence (SEQ ID NO:9)

```
AGTGCGGCAATCACACAGGAAGGAGCAGCTCCGGCCGCTATGTTACATCCAGAGAAATGGCC
TCGACCTGCGACACAACGACTTATTGACCCGGCAGTTGAAAAAGAGTTGATGCTCTGTTAA
AACAGTTATCTGTTGAAGAAAAGTAGGGCAAGTTATACAGGGTGATATTGGGACAATTACA
CCAGAAGACCTGCGCAAATATCCACTAGGTTCTATTTTAGCCGGAGGAGATAGCGGCCCGAA
TGGAGATGATCGTGCTCCTCCAAAGGAGTGGCTTGATCTAGCTGATGCTTTTTACCGTGTAA
GTTTAGAAAAACGGCCAGGCCATACCCCGATACCAGTGCTTTTTGGCATTGATGCAGTTCAT
GGACATAACAATATCGGGTCTGCGACAATTTTCCCTCACAATATTGCACTTGGAATGACCCG
TGATCCAGAACTTCTACGAAGAATTGGTGAGGTAACAGCTGAAGAAATGGCTGCCACGGGAA
TTGATTGGACATTTGCGCCTGCACTGTCTGTTGTGAGAGATGATCGATGGGGACGAACGTAT
GAAGGCTTCTCAGAAGATCCAGAAATTGTAGCTTCTTATTCAGCAGCAATTGTGGAAGGCTT
TCAGGGTAAATATGGTTCTAAGGATTTTATGGCGCCGGGTCGCGCGGTAGCGTGCGCAAAGC
ACTTCTTAGCTGATGGTGGAACAGATCAAGGACGCGATCAGGGAGATGCACGCATTTCAGAA
GACGAACTAATTCGCATTCATAATGCTGGATACCCTCCTGCGATTGACGCAGGAGTGCTGAC
AGTAATGGCTTCTTTTTCATCCTGGCAGGGGATTAAACACCATGGCCATAAACAACTTTTAA
CAGATGTATTAAAAGGACAAATGGGGTTTAATGGATTTATTGTGGGGATTGGAATGCTCAT
GACCAAGTACCGGGCTGTACTAAATTTAATTGTCCAACATCTCTTATTGCGGGTTTAGATAT
GTATATGGCCGCCGATTCCTGGAAGCAGCTGTACGAAAACACCTTAGCACAAGTGAAAGATG
GTACTATTCCTATGGCACGTCTAGATGATGCCGTAAGACGAATCTTGCGAGTCAAGGTGTTG
GCTGGCTTATTCGAGAAACCTGCGCCAAAAGATCGTCCGGGGTTACCAGGCCTTGAAACACT
AGGATCACCTGAACATAGAGCCGTAGGCCGTGAAGCTGTTCGAAAAAGCCTAGTTCTTCTTA
AAAATGATAAAGGTACCCTTCCACTGTCACCAAAGGCTAGAGTATTAGTTGCAGGTGACGGA
GCAGATAATATTGGCAAACAGTCGGGGGCTGGACGATTAGTTGGCAAGGAACTGGAAACCG
TAACGATGAATTTCCGGGTGCTACATCCATTTTAGGTGGGATTCGAGACGCTGTAGCTGATG
CAGGAGGGTCCGTAGAATTTGATGTAGCGGGTCAGTATAAAACAAAACCTGATGTAGCTATT
GTTGTTTTTGGCGAAGAACCTTATGCTGAGTTTCGTGGAGATGTGGAGACACTGGAATATCA
ACCAGATCAAAAACAAGATCTTACCCTACTCAAGAAACTGAAAGATCAGGGAATACCTGTTG
TTGCTGTTTTCCTTTCTGGACGACCGATGTGGGTTAATCCTGAACTTAATGCCAGCGATGCT
TTCGTTGCAGCATGGCTTCCTGGCACAGAAGGTGGCGGTGTGGCGGATGTATTGTTTACAGA
CAAAGCGGGAAAAGTACAACATGATTTTGCAGGAAAATTGTCATATAGTTGGCCGCGTACGG
CAGCCCAGACAACAGTTAACCGTGGTGATGCAGATTATAATCCGTTATTTGCGTATGGTTAC
GGTTTAACGTACAAAGATAAATCGAAAGTGGGCACTCTACCTGAAGAAAGTGGAGTACCGGC
TGAAGCGCGACAGAATTGA
```

FIG. 5B
BG-2 protein sequence (SEQ ID NO:10)

```
SAAITQEGAAPAAMLHPEKWPRPATQRLIDPAVEKRVDALLKQLSVEEKVGQVIQGDIGTIT
PEDLRKYPLGSILAGGDSGPNGDDRAPPKEWLDLADAFYRVSLEKRPGHTPIPVLFGIDAVH
GHNNIGSATIFPHNIALGMTRDPELLRRIGEVTAEEMAATGIDWTFAPALSVVRDDRWGRTY
EGFSEDPEIVASYSAAIVEGFQGKYGSKDFMAPGRAVACAKHFLADGGTDQGRDQGDARISE
DELIRIHNAGYPPAIDAGVLTVMASFSSWQGIKHHGHKQLLTDVLKGQMGFNGFIVGDWNAH
DQVPGCTKFNCPTSLIAGLDMYMAADSWKQLYENTLAQVKDGTIPMARLDDAVRRILRVKVL
AGLFEKPAPKDRPGLPGLETLGSPEHRAVGREAVRKSLVLLKNDKGTLPLSPKARVLVAGDG
ADNIGKQSGGWTISWQGTGNRNDEFPGATSILGGIRDAVADAGGSVEFDVAGQYKTKPDVAI
VVFGEEPYAEFRGDVETLEYQPDQKQDLTLLKKLKDQGIPVVAVFLSGRPMWVNPELNASDA
FVAAWLPGTEGGGVADVLFTDKAGKVQHDFAGKLSYSWPRTAAQTTVNRGDADYNPLFAYGY
GLTYKDKSKVGTLPEESGVPAEARQN
```

MULTI-CELLULASE ENZYME COMPOSITIONS FOR HYDROLYSIS OF CELLULOSIC BIOMASS

CROSS-REFERENCE TO RELATED APPLICATIONS

This application claims the benefit of U.S. Provisional Application 61/263,267 filed Nov. 20, 2009 the contents of which are hereby incorporated by reference in its entirety.

FIELD OF THE INVENTION

The invention relates to multi-cellulase enzyme compositions used for the hydrolysis of cellulosic biomass and methods of using the same. More specifically, the present invention relates to multi-cellulase enzyme compositions which include cellobiohydrolases (CBHs), endoglucanases (EGs) and β-glucosidases (BGLs) and use of the compositions in the enzymatic hydrolysis of cellulose to produce fermentable sugars.

REFERENCE TO SEQUENCE LISTING

The "Sequence Listing" submitted electronically concurrently herewith pursuant to 37C.F.R. §1.821 in computer readable form (CRF) via EFS-Web as file name CX3-035WO1_ST25.txt. is incorporated herein by reference. The electronic copy of the Sequence Listing was created on Nov. 15, 2010, and the size on disk is 32.0 Kbytes.

BACKGROUND OF THE INVENTION

Cellulosic biomass is a significant renewable resource for the generation of sugars. Fermentation of these sugars can yield commercially valuable end-products, including biofuels and chemicals that are currently derived from petroleum. While the fermentation of simple sugars to ethanol is relatively straightforward, the efficient conversion of cellulosic biomass to fermentable sugars such as glucose is challenging. See, e.g., Ladisch et al., 1983, *Enzyme Microb. Technol.* 5:82. Cellulosic biomass may be pretreated chemically, mechanically or in other ways to increase the susceptibility of cellulose to hydrolysis. Such pretreatment may be followed by the enzymatic conversion of cellulose to glucose, cellobiose, cello-oligosaccharides and the like, using enzymes that specialize in breaking down the β-1-4 glycosidic bonds of cellulose. These enzymes are collectively referred to as "cellulases".

Cellulases are divided into three sub-categories of enzymes: 1,4-β-D-glucan glucanohydrolase ("endoglucanase" or "EG"); 1,4-β-D-glucan cellobiohydrolase ("exoglucanase", "cellobiohydrolase", or "CBH"); and 3-D-glucoside-glucohydrolase ("β-glucosidase", "cellobiase" or "BG"). Endoglucanases randomly attack the interior parts and mainly the amorphous regions of cellulose. Exoglucanases incrementally shorten the glucan molecules by binding to the glucan ends and releasing mainly cellobiose units from the ends of the cellulose polymer. β-glucosidases split the cellobiose, a water-soluble β-1,4-linked dimer of glucose, into two units of glucose. In order to efficiently convert cellulosic biomass to fermentable sugars, a complete cellulase system comprising components from each class of cellulases (CBH, EG and BG) is required, and it is well known in the art that the individual cellulase components are less effective at hydrolyzing cellulose comprising substrates than the combination of the three components.

Although cellulase compositions have been previously described, there remains a need for new and improved cellulase compositions for use in processing cellulosic biomass and for cellulase compositions that contribute to the reduction in cost and increase in efficiency of producing biofuels and other commercially valuable compounds.

SUMMARY OF THE INVENTION

In some aspects the invention relates to a multi-cellulase enzyme composition for the enzymatic hydrolysis of cellulose said composition comprising a cellobiohydrolase (CBH) enzyme, an endoglucanases (EG) enzyme and a β-glucosidase (BG) enzyme. In one aspect, the enzyme composition will comprise a CBH enzyme comprising at least 90% sequence identity to SEQ ID NO:2, an EG enzyme comprising at least 90% sequence identity to SEQ ID NO:4 or SEQ ID NO:6, and a BG enzyme comprising at least 90% sequence identity to SEQ ID NO:8 or SEQ ID NO: 10. In some embodiments, the CBH enzyme has at least 95% sequence identity to SEQ ID NO:2, the EG enzyme has at least 95% sequence identity to SEQ ID NO:4 or SEQ ID NO:6, and the BG enzyme has at least 95% sequence identity to SEQ ID NO:8 or SEQ ID NO:10. In other embodiments, the multi-cellulase enzyme compositions further comprise accessory enzymes.

In some aspects, the invention relates to a method of hydrolyzing a cellulose substrate to a fermentable sugar comprising a) contacting an aqueous slurry comprising a cellulose substrate with a multi-cellulase enzyme composition comprising a CBH enzyme comprising at least 95% sequence identity to SEQ ID NO: 2, an EG enzyme comprising at least 95% sequence identity to SEQ ID NO:4 or SEQ ID NO:6 and a BG enzyme comprising at least 95% sequence identity to SEQ ID NO:8 or SEQ ID NO:10 and b) hydrolyzing the slurry under sufficient conditions to produce a hydrolysis product comprising fermentable sugars comprising glucose. In some embodiments, the slurry comprising a cellulose substrate is obtained from agricultural biomass. In further embodiments, the biomass is obtained from wheat straw, corn stover, oat straw, barley straw, rice straw, miscanthus, switch grass, bagasse, soybean stover or combinations thereof. In other embodiments, the cellulose substrate is pretreated prior to the contacting step. In additional embodiments, the method comprises recovering or isolating the fermentable sugars. In further embodiments, additional steps include fermenting the fermentable sugars with a fermenting microorganism under sufficient conditions to obtain an end-product, such as but not limited to, fuels (such as, but not limited to ethanol or butanol), amino acids, organic acids, solvents, animal feed supplements and the like.

BRIEF DESCRIPTION OF THE FIGURES

FIGS. 1A and B show the polynucleotide sequence (SEQ ID NO:1) and encoded protein sequence (SEQ ID NO:2) of a CBH2.

FIGS. 2A and B show the polynucleotide sequence (SEQ ID NO:3) and encoded protein sequence (SEQ ID NO:4) of EG-1.

FIGS. 3A and B show the polynucleotide sequence (SEQ ID NO:5) and encoded protein sequence (SEQ ID NO:6) of EG-2.

FIGS. 4A and B show the polynucleotide sequence (SEQ ID NO: 7) and encoded protein sequence (SEQ ID NO: 8) of BG-1.

FIGS. 5A and B show the polynucleotide sequence (SEQ ID NO: 9) and encoded protein sequence (SEQ ID NO:10) of BG-2.

DETAILED DESCRIPTION OF THE INVENTION

I. Definitions

The following definitions are provided to assist the reader. Unless otherwise defined, all terms of art are intended to have the meanings commonly understood by those of skill in the molecular biology and microbiology arts. In some cases, terms with commonly understood meanings are defined herein for clarity and/or for ready reference, and the inclusion of such definitions herein should not necessarily be construed to represent a substantial difference over the definition of the term as generally understood in the art.

The term "cellulase" refers to a category of enzymes capable of hydrolyzing cellulose (β-1,4-glucan or β-D-glucosidic linkages) to shorter oligosaccharides, cellobiose and/or glucose.

The term "β-glucosidase", "cellobiase" or BG used interchangeably herein means a β-D-glucoside glucohydrolase which catalyzes the hydrolysis of a sugar dimer, including but not limited to cellobiose, with the release of a corresponding sugar monomer. In one embodiment, a β-glucosidase is a β-glucosidase glucohydrolase of the classification E.C. 3.2.1.21 which catalyzes the hydrolysis of cellobiose to glucose. Some of the β-glucosidases have the ability to also hydrolyze β-D-galactosides, β-L-arabinosides and/or β-D-fucosides and further some β-glucosidases can act on α-1,4-substrates such as starch. β-glucosidase activity may be measured by methods well known in the art, including the assays described hereinbelow.

"Cellulolytic activity" encompasses exoglucanase activity (CBH), endoglucanase (EG) activity and/or β-glucosidase (BG) activity.

The term "exoglucanase" or "exo-cellobiohydrolase" refers to a group of cellulase enzymes classified as E.C. 3.2.1.91. These enzymes hydrolyze cellobiose from the reducing or non-reducing end of cellulose. "CBH1" is a carbohydrate active enzyme known as a glycohydrolase Family 7 enzyme classified as EC 3.2.1.91 and "CBH2" is a carbohydrate active enzyme known as a glycohydrolase Family 6 enzymes classified as EC 3.2.1.91.

The term "endoglucanase" or "EG" refers to a group of cellulase enzymes classified as E.C. 3.2.1.4. These enzymes hydrolyze internal β-1,4 glucosidic bonds of cellulose.

As used herein the phrase "multi-cellulase enzyme composition" means a non-naturally occurring cellulase composition comprising a CBH, EG and BG according to the invention produced by combining the component cellulolytic enzymes which are either obtained from various microbial sources, are variants of wildtype cellulolytic enzymes and/or modifying an organism to express a heterologous component cellulolytic enzyme.

As used herein, the term "isolated" refers to a nucleic acid, polynucleotide, polypeptide, protein, or other component that is partially or completely separated from components with which it is normally associated (other proteins, nucleic acids, cells, synthetic reagents, etc.).

The term "wildtype" as applied to a polypeptide (protein) means a polypeptide (protein) expressed by a naturally occurring microorganism such as bacteria or filamentous fungus. As applied to a microorganism, the term "wildtype" refers to the native, non-recombinant micro-organism.

A nucleic acid (such as a polynucleotide), a polypeptide, or a cell is "recombinant" when it is artificial or engineered, or derived from or contains an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

The term "heterologous" refers to any polynucleotide that is introduced into a host cell by laboratory techniques, and includes polynucleotides that are removed from a host cell, subjected to laboratory manipulation, and then reintroduced into a host cell. Heterologous protein expression means the expression of a protein from a heterologous polynucleotide.

The term "culturing" or "cultivation" refers to growing a population of microbial cells under suitable conditions in a liquid or solid medium. In some embodiments, culturing refers to fermentative bioconversion of a cellulosic substrate to an end-product.

The term "contacting" refers to the placing of a respective enzyme or enzyme composition in sufficiently close proximity to a respective substrate to enable the enzyme to convert the substrate to a product. Those skilled in the art will recognize that mixing a solution of the enzyme with the respective substrate will effect contacting.

As used herein the term "transformed" or "transformation" used in reference to a cell means a cell has a non-native nucleic acid sequence integrated into its genome or as an episomal plasmid that is maintained through multiple generations.

The term "operably linked" refers herein to a configuration in which a control sequence is appropriately placed at a position relative to the coding sequence of the DNA sequence such that the control sequence influences the expression of a polypeptide.

When used herein, the term "coding sequence" is intended to cover a nucleotide sequence, which directly specifies the amino acid sequence of its protein product. The boundaries of the coding sequence are generally determined by an open reading frame, which usually begins with the ATG start codon. The coding sequence typically includes a DNA, cDNA, and/or recombinant nucleotide sequence.

As used herein, the term "expression" includes any step involved in the production of the polypeptide including, but not limited to, transcription, post-transcriptional modification, translation, post-translational modification, and secretion.

The term "expression vector" refers herein to a DNA molecule, linear or circular, that comprises a segment encoding a polypeptide of the invention, and which is operably linked to additional segments that provide for its transcription.

The term "cellobiose" has its ordinary meaning and refers to a disaccharide with the formula $[HOCH_2CHO(CHOH)_3]_2O$.

A polypeptide is "enzymatically active" when it has exoglucanase activity (CBH), endoglucanase (EG) activity and/or β-glucosidase activity.

The term "pre-protein" refers to a secreted protein with an amino-terminal signal peptide region attached. The signal peptide is cleaved from the pre-protein by a signal peptidase prior to secretion to result in the "mature" or "secreted" protein.

The term "fermentable sugar" means a simple sugar such as monosaccharides and disaccharides that can be converted by a microorganism in an enzymatic reaction to an end-product. Non-limiting examples of fermentable sugars include C5 and C6 sugars, such as, but not limited to glucose, xylose, mannose, arabinaose, galactose, rhamnose and fructose.

The term "aqueous slurry" means a mixture of cellulose containing biomass and liquid such as water. The terms "mash" and "feedstock" can be used interchangeability with aqueous slurry.

The term "biomass" refers to living or dead biological material that contains a polysaccharide substrate, such as, for example, cellulose, starch, and the like.

The term "pretreatment" as used herein means a process used to disrupt the cellulose structure of a biomass substrate which is carried out prior to hydrolysis with the multi-cellulase enzyme compositions of the invention. The pretreatment process may include various methods such as mechanical, physical and/or biological processes.

The phrase "degree of synergy (DS)" as used herein means greater than additive amounts and is measured by the ratio of activity exhibited by enzyme mixtures divided by the sum of the activity of separate enzyme components under the same conditions (e.g., pH, temperature, time, and/or protein concentration). In some embodiments, the DS will be greater than 1.0, greater than 1.25, greater than 1.5, great than 1.75, greater than 2.0, greater than 2.25, and greater than 2.5.

The terms "percent (%) identity," "sequence identity," and "percent (%) identical" are used interchangeably herein to refer to the percent amino acid sequence identity that is obtained by ClustalW analysis (version W 1.8 available from European Bioinformatics Institute, Cambridge, UK), counting the number of identical matches in the alignment and dividing such number of identical matches by the length of the reference sequence, and using the following default ClustalW parameters to achieve slow/accurate pairwise optimal alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art. See e.g., Dayhoff et al. (1978), "A model of evolutionary change in proteins"; "Atlas of Protein Sequence and Structure," Vol. 5, Suppl. 3 (Ed. M.O. Dayhoff), pp. 345-352, *Natl. Biomed. Res. Round.*, Washington, D.C.; and Henikoff et al. (1992) *Proc. Natl. Acad. Sci. USA*, 89:10915-10919, both of which are incorporated herein by reference. The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm, e.g., gapped BLAST 2.0, described in Altschul, et al. (1997) *Nucleic Acids Res.*, 25:3389-3402 (incorporated herein by reference), and made available to the public at the National Center for Biotechnology Information Website. Optimal alignments, including multiple alignments can be prepared using readily available programs such as PSI-BLAST, which is described by Altschul, et al. (1997) *Nucleic Acids Res.*, 25:3389-3402 and which is incorporated herein by reference.

II. Multi-Cellulase Enzyme Compositions

The enzyme compositions according to the invention include a mixture of CBH, EG and BG cellulase enzymes. A CBH enzyme which comprises one component of the composition will have a protein sequence comprising at least 90%, (e.g. at least 90%, 91%, 92%, 93%, 94%, 95%, 96%, 97%, 98%, and 99%) amino acid sequence identity to the sequence of SEQ ID NO:2. In some aspects, the CBH of the invention will comprise the sequence of SEQ ID NO:2. In some aspects, the CBH will have CBH2 activity. In some aspects, the CBH will optionally have at least 1, at least 2, at least 3, at least 4, at least 5, at least 6, at least 7 and at least 8 further amino acid substitutions as compared to SEQ ID NO: 2. In one embodiment, the CBH enzyme of the invention comprises at least 95% sequence identity to SEQ ID NO: 2 and comprises a substitution at a position corresponding to A30, A118, S122, S175, I180, V183, G202, Q206, G216, V219, D221, S233, P234T241, Q253, N274, S299, V324, Q378, and/or S395 when optimally aligned with SEQ ID NO: 2. In some embodiments, the substitution corresponds to A30T, A118R, S122V/H, S175Q/L, I180K/C, V183G, G202F/Y, Q206L, G216K, V219E/R, D221L, S233C, P234ST241R/K, Q253M/A/S, N274K/P, V324H/F and/or S395T. In other embodiments, the substitution corresponds to position 201 and/or position 234 when optimally aligned with SEQ ID NO:2. In some embodiments, the CBH will comprise at least 97% sequence identity with SEQ ID NO:2 and optionally have one, two, three or four further substitutions. In some embodiments, the CBH will have the amino acid sequence of SEQ ID NO:2.

An EG which comprises one component of the composition will have an amino acid sequence comprising at least 90%, (e.g. at least 90%, 91%, 92%, 93%, 94%, 95%, 96%, 97%, 98%, and 99%) amino acid sequence identity to the sequence of SEQ ID NO:4 or SEQ ID NO:6. In some aspects, the EG of the invention has an amino acid sequence comprising at least 95% sequence identity to SEQ ID NO: 4 and/or SEQ ID NO:6. In some embodiments, the EG will be EG-1 and in other embodiments, the EG will be EG-2. In some aspects, the EG will optionally have at least 1, at least 2, at least 3, at least 4, at least 5, at least 6, at least 7, at least 8, at least 9, at least 10, at least 11, at least 12, at least 13 and at least 14 further amino acid substitutions when optimally aligned with SEQ ID NO:4 or SEQ ID NO: 6. In one embodiment, the EG enzyme of the invention comprises at least 97% sequence identity to SEQ ID NO: 4 and optionally comprises a substitution at a position corresponding to S10, T12, Q43, V48, N68, Q78, L79, T81, V82, M98, S152, S185, and/or Q206 when optimally aligned with SEQ ID NO: 4. In one embodiment, the EG enzyme of the invention comprises at least 97% sequence identity to SEQ ID NO:4 and optionally comprises a substitution at a position corresponding to S10W, T12V/I, Q43R, V48K, N68I, Q78K, L79I, T81I/K, V82I, M98V, S152M, S185Q/V, and/or Q206E, when optimally aligned with SEQ ID NO:4.

A BG which comprises one component of the composition will have a protein sequence comprising at least 90%, (e.g. at least 90%, 91%, 92%, 93%, 94%, 95%, 96%, 97%, 98%, and 99%) amino acid sequence identity to the sequence of SEQ ID NO:8 or SEQ ID NO: 10. In some aspects, the BG of the invention has a protein sequence comprising at least 95% sequence identity to SEQ ID NO: 8 and/or SEQ ID NO:10. In some embodiments, the BG will be BG-1 and in other embodiments the BG will be BG-2. In some aspects, the BG will optionally have at least 1, at least 2, at least 3, at least 4, at least 5, at least 6, at least 7, at least 8, at least 9, at least 10, at least 11, at least 12, at least 13 and at least 14 further amino acid substitutions when optimally aligned with SEQ ID NO:8 or SEQ ID NO: 10. In one embodiment, the BG enzyme of the invention comprises at least 97% sequence identity to SEQ ID NO:8 when optimally aligned with SEQ ID NO: 8 and optionally comprises at least 1, at least 2, at least 3, at least 4, at least 5, and at least 6 further substitutions. In one embodiment, the BG enzyme of the invention comprises at least 97% sequence identity to SEQ ID NO:10 and optionally at least 1, at least 2, at least 3, at least 4, at least 5, and at least 6 further substitutions when optimally aligned with SEQ ID NO:10.

In some aspects, the mixture of CBH:EG:BG comprises a CBH comprising at least 95% sequence identity to SEQ ID NO: 2; an EG comprising at least 95% sequence identity to SEQ ID NO:4 and/or SEQ ID NO: 6 and a BG comprising at least 95% sequence identity to SEQ ID NO:8 and/or SEQ ID NO:10. In some aspects, the mixture of CBH:EG:BG comprises a CBH comprising at least 98% sequence identity to SEQ ID NO: 2; an EG comprising at least 98% sequence identity to SEQ ID NO:4 and/or SEQ ID NO: 6 and a BG comprising at least 98% sequence identity to SEQ ID NO:8 and/or SEQ ID NO:10. In some embodiments, the cellulase mixture includes the CBH of SEQ ID NO: 2, the EG of SEQ ID NO: 4 and/or SEQ ID NO: 6, and the BG of SEQ ID NO.8 and/or SEQ ID NO:10.

According to the present invention, the CBH enzyme component within the enzyme composition comprising a CBH, EG and BG may be present at greater than or equal to 30 wt % and less than 98 wt % or, any wt % between. The EG enzyme component within the enzyme composition comprising a CBH, EG and BG may be present at greater than or equal to 1.0 wt % and less than 45 wt % or, any wt % between. The BG enzyme component within the enzyme composition comprising a CBH, EG and BG may be present at greater than or equal to 0.1 wt % and less than 45 wt % or, any wt % between. According to the present invention in some embodiments, the CBH enzyme component within the enzyme composition comprising a CBH, EG and BG may be present at greater than or equal to 35 wt % and less than 95 wt %; greater than or equal to 50 wt % and less than 90 wt % or, any wt % between. The EG enzyme component within the enzyme composition comprising a CBH, EG and BG may be present at greater than or equal to 1.0 wt % and less than 20 wt %; greater than or equal to 1.0 wt % and less than 15 wt % or, any wt % between. The BG enzyme component within the enzyme composition comprising a CBH, EG and BG may be present at greater than or equal to 0.5 wt % and less than 20 wt %; great than or equal to 1.0 wt % or less than 15 wt % or, any wt % between.

According to one embodiment, the CBH enzyme component within the enzyme composition comprising a CBH, EG and BG may be present at greater than or equal to 30, 35, 40, 45, 50, 55, 60, 65, or 70 wt % and less than 98, 95, 90, 85, or 80 wt %. The EG enzyme component within the enzyme composition comprising a CBH, EG and BG may be present at greater than or equal to 1, 5, 10 or 15 wt % and less than 45, 40, 35, 30, 25, 20, 15 wt %. The BG enzyme component within the enzyme composition comprising a CBH, EG and BG may be present at greater than or equal to 0.1, 0.5, 1, 2, 5, 10, or 15 wt % and less than 45, 40, 35, 30, 25, or 20 wt %. In some embodiments, the CBH enzyme component/the EG enzyme component/and the BG enzyme component of the composition on a wt % will approximately 60-98% CBH; approximately 1-25% EG and approximately 0.1 to 15% BG.

The effective amount of the multi-cellulase enzyme composition may vary depending on the biomass substrate and the conditions. However, an effective amount will generally be between about 0.01% and 25% by dry weight (e.g., between about 0.01% and 25%, between about 0.01% and 20%, between about 0.01% and 15%, between about 0.01% and 10%, between about 0.02 and 5%, between about 0.02% and 2%) of the cellulosic material. In some embodiments, the ratio of CBH:EG:BG on a % weight basis is in the range of 70:1:1, in the range of 50:1:1, in the range of 40:1:1, in the range of 20:1:1, in the range of 10:1:1, in the range of 8:1:1; in the range of 4:1:1, in the range of 2:1:1, in the range of 1:1:1, in the range of 4:1:2, and also in the range of 2:1:2.

In some embodiments, the multi-cellulase enzyme composition may include accessory enzymes. Accessory enzymes include but are not limited to enzymes such as other cellulases, for example CBHs (e.g. CBH1 and CBH2), EGs (e.g., EG1s, EG2s, EG4s, and EG5s), BGs, (e.g., BG1s, BG2s, and BG3s), hemicellulases (such as xylanases, mannanases and arabinofuranosidases), ligninases, lipases, esterases (e.g. ferulic acid esterases and coumaric acid estereases), proteases, amylases, glucoamylases, and pectinases, Sources of these enzyme are well known in the art. For example, CBH1 enzymes are known in the art and may be obtained, for example from, strains of *Hyprocrea, Trichoderma, Talaromyces, Thermoascus, Penicillum,* and *Aspergillus*. One specific example includes the CBH1 from *Trichoderma reesei* (See, Genpept Accession No. CAH10320). CBH2 enzymes are known in the art and may be obtained, for example from strains of *Hyprocrea, Trichoderma, Chrysosporium, Acremonium, Talaromyces, Thermoascus, Penicillum, Humicola,* and *Aspergillus*. One specific example includes the CBH2 from *Trichoderma reesei* (See, Genpept Accession No. AAA34210). EG1 enzymes are known in the art and may be obtained, for example from strains of *Hyprocrea, Trichoderma, Chrysosporium, Penicillum* and *Aspergillus*. One specific example includes the EG1 from *Trichoderma reesei* (See, Genpept Accession No. AAA34212). EG2 enzymes are known in the art and may be obtained, for example from strains of *Hyprocrea, Trichoderma, Cryptococcus, Thermoascus, Trametes, Penicillum, Humicola,* and *Aspergillus*. One specific example includes the EG2 from *Trichoderma reesei* (See, Genpept Accession No. AAA34213). BG enzymes are known in the art and may be obtained, for example from strains of *Hyprocrea, Trichoderma, Chrysosporium, Acremonium, Talaromyces, Thermoascus, Penicillum, Humicola,* and *Aspergillus*. One specific example includes the CBH2 from *Trichoderma reesei* (See, Genpept Accession No. AAA34210). In addition, accessory enzymes may be obtained from commercial suppliers; cloned genes expressing the enzymes, fermentation broth resulting from the production or secretion of the enzymes into the media or broth and cell lysates of strains encompassing genes expressing the enzymes.

In some embodiments, the accessory enzymes will be cellulase enzymes and specifically CBH1 enzymes. In some embodiments, the accessory enzymes will be hemicellulases, xylanases, and/or esterases. In some embodiments, the accessory enzymes will comprise between about 1% and 35% of the multi-cellulase enzyme compositions. In some embodiments, the accessory enzymes will not comprise more than about 5%, more than about 10%, more than about 20%, more than about 25% or more than about 30% of the enzyme composition.

One of skill in the art will readily appreciate that the multi-cellulase enzyme compositions of the present invention may be used in the form of an aqueous solution or a solid concentrate. When aqueous solutions are employed, the solution can easily be diluted to allow accurate concentrations. A concentrate can be in any form recognized in the art including, for example, liquids, emulsions, suspensions, gel, pastes, granules, powders, an agglomerate, a solid disk, as well as other forms that are well known in the art.

The multi-cellulase enzyme compostions of the present invention may include or be mixed with optional ingredients such as a buffer, a surfactant, and/or a scouring agent. A buffer may be used with the enzyme composition to maintain a desired pH within the solution. Suitable buffers are well known in the art. A surfactant may further be used in combination with the cellulase composition. Suitable surfactants include any surfactant compatible with the cellulases and accessory enzymes being utilized. Exemplary surfactants include an anionic, a non-ionic, and ampholytic surfactants. Suitable anionic surfactants include, but are not limited to, linear or branched alkylbenzenesulfonates; alkyl or alkenyl ether sulfates having linear or branched alkyl groups or alkenyl groups; alkyl or alkenyl sulfates; olefinsulfonates; alkanesulfonates, and the like. Suitable counter ions for anionic surfactants include, for example, alkali metal ions, such as sodium and potassium; alkaline earth metal ions, such as calcium and magnesium; ammonium ion; and alkanolamines having from 1 to 3 alkanol groups of carbon number 2 or 3 Ampholytic surfactants suitable for use in the practice of the present invention include, for example, quaternary ammonium salt sulfonates, betaine-type ampholytic surfactants, and the like. Suitable nonionic surfactants generally include polyoxalkylene ethers, as well as higher fatty acid alkanolamides or alkylene oxide adduct thereof, fatty acid glycerine monoesters, and the like. Mixtures of surfactants can also be employed as is known in the art.

III. Methods for Making the Multi-Cellulase Enzyme Compositions

Methods for making the polypeptides comprising the multi-cellulase enzyme compositions are well known in the art and classical methods and modern molecular biology techniques can be utilized in this regard. Reference is also made to co-pending applications PCT/US10/47324 filed Aug. 31, 2010 disclosing various CBH2 enzymes encompassed by the present invention; U.S. Ser. No. 12/751,985 filed Mar. 31, 2010 disclosing various EG enzymes encompassed by the present invention; and U.S. Ser. No. 12/816,989 filed Jun. 16, 2010 disclosing various BG enzymes encompassed by the invention. Each of these references is incorporated by reference herein in their entirety. Recombinant methods will allow the construction of various microbial strains that contain either a mixture of DNA encoding the cellulase enzymes or contain DNA encoding individual cellulase enzymes encompassed by the present invention.

Briefly, a CBH, EG and/or BG protein may be made by culturing a host cell comprising a vector comprising a nucleic acid sequence for example encoding a CBH enzyme having a protein sequence comprising at least 90%, (e.g. at least 90%, 91%, 92%, 93%, 94%, 95%, 96%, 97%, 98%, 99% and even 100%) amino acid sequence identity to the sequence of SEQ ID NO:2; an EG having a protein sequence comprising at least 90%, (e.g. at least 90%, 91%, 92%, 93%, 94%, 95%, 96%, 97%, 98%, 99% and even 100%) amino acid sequence identity to the sequence of SEQ ID NO:4 and/or SEQ ID NO:6; and/or a BG having protein sequence comprising at least 90%, (e.g. at least 90%, 91%, 92%, 93%, 94%, 95%, 96%, 97%, 98%, 99% and even 100%) amino acid sequence identity to the sequence of SEQ ID NO:8 and/or SEQ ID NO:10 operably linked to a heterologous promoter, under conditions in which the cellulase protein is expressed. In some embodiments, the CBH will be encoded by a polynucleotide having at least 90% (at least 91%, 92%, 93%, 94%, 95%, 96%, 97%, 98%, 99% and even 100% sequence identity to the polynucleotide of SEQ ID NO: 1. In some embodiments, the EG will be encoded by a polynucleotide having at least 90% (at least 91%, 92%, 93%, 94%, 95%, 96%, 97%, 98%, 99% and even 100% sequence identity to the polynucleotide of SEQ ID NO: 3 or SEQ ID NO: 5. In some embodiments, the BG will be encoded by a polynucleotide having at least 90% (at least 91%, 92%, 93%, 94%, 95%, 96%, 97%, 98%, 99% and even 100% sequence identity to the polynucleotide of SEQ ID NO: 7 or SEQ ID NO: 9. Generally the expressed protein comprises a signal peptide. In some embodiments, the cellulase polypeptide includes additional sequences which do not alter the activity of a cellulase. For example, the cellulase may be linked to an epitope tag or to other sequence useful in purification.

Those having ordinary skill in the art will readily appreciate that due to the degeneracy of the genetic code, a multitude of nucleotide sequences encoding the cellulase polypeptides of the present invention exist. The invention contemplates and provides each and every possible variation of nucleic acid sequence encoding a polypeptide of the invention that could be made by selecting combinations based on possible codon choices. Nucleic acid constructs of the present invention comprise a vector, such as, a plasmid, a cosmid, a phage, a virus, a bacterial artificial chromosome (BAC), a yeast artificial chromosome (YAC), and the like, into which a nucleic acid sequence of the invention has been inserted. Polynucleotides of the present invention can be incorporated into any one of a variety of expression vectors suitable for expressing a polypeptide. Any vector that transduces genetic material into a cell, and, if replication is desired, which is replicable and viable in the relevant host can be used. In one preferred aspect the construct further comprises regulatory sequences, including, for example, a promoter, operably linked to the protein encoding sequence. Large numbers of suitable vectors and promoters are known to those of skill in the art.

Polynucleotides encoding the cellulases can be prepared using methods that are well known in the art. Typically, oligonucleotides of up to about 40 bases are individually synthesized, then joined (e.g., by enzymatic or chemical ligation methods, or polymerase-mediated methods) to form essentially any desired continuous sequence. For example, polynucleotides of the present invention can be prepared by chemical synthesis using, for example, the classical phosphoramidite method described by Beaucage, et al., 1981, *Tetrahedron Letters,* 22:1859-69, or the method described by Matthes, et al., 1984, *EMBO J.* 3:801-05, both of which are incorporated herein by reference. These methods are typically practiced in automated synthetic methods. According to the phosphoramidite method, oligonucleotides are synthesized, e.g., in an automatic DNA synthesizer, purified, annealed, ligated and cloned in appropriate vectors.

In addition, essentially any nucleic acid can be custom ordered from any of a variety of commercial sources, such as The Midland Certified Reagent Company (Midland, Tex.), The Great American Gene Company (Ramona, Calif.), ExpressGen Inc. (Chicago, Ill.), Operon Technologies Inc.

(Alameda, Calif.), and many others. Polynucleotides may also be synthesized by well-known techniques as described in the technical literature. See, e.g., Carruthers, et al., 1982, *Cold Spring Harbor Symp. Quant. Biol.*, 47:411-18 and Adams et al., 1983, *J. Am. Chem. Soc.* 105:661, both of which are incorporated herein by reference. Double stranded DNA fragments may then be obtained either by synthesizing the complementary strand and annealing the strands together under appropriate conditions, or by adding the complementary strand using DNA polymerase with an appropriate primer sequence.

General texts that describe molecular biological techniques which are useful herein, including the use of vectors, promoters, protocols sufficient to direct persons of skill through in vitro amplification methods, including the polymerase chain reaction (PCR) and the ligase chain reaction (LCR), and many other relevant methods, include for example, Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel"), all of which are incorporated herein by reference.

Engineered (recombinant) host cells may be used to produce the cellulase polypeptides according to the invention. A genetically modified or recombinant host cell includes the progeny of said host cell that comprises a cellulase polynucleotide which encodes a cellulase polypeptide of the invention. In some embodiments, the genetically modified or recombinant host cell is a eukaryotic cell. Suitable eukaryotic host cells include, but are not limited to fungal cells (e.g., filamentous fungal cells) and algal cells. Cells (e.g., fungi) that have been mutated or selected to have low protease activity are particularly useful for expression.

In some embodiments, the filamentous fungal host cell is of the *Aspergillus* species, *Ceriporiopsis* species, *Chrysosporium* species, *Corynascus* species, *Fusarium* species, *Humicola* species, *Myceliophthora* species, *Neurospora* species, *Penicillium* species, *Tolypocladium* species, *Thielavia* species, *Tramates* species, or *Trichoderma* species.

In the present invention a yeast host cell may be a cell of a species of, but not limited to *Candida*, *Hansenula*, *Saccaromyces*, *Schizosaccharomyces*, *Pichia*, *Kluyveromyces*, and *Yarrowia*. In some embodiments of the invention, the yeast cell is *Hansenula polymorpha*, *Saccharomyces cerevisiae*, *Saccaromyces carlsbergensis*, *Saccharomyces diastaticus*, *Saccharomyces norbensis*, *Saccharomyces kluyveri*, *Schizosaccharomyces pombe*, *Pichia pastoris*, *Pichia finlandica*, *Pichia trehalophila*, *Pichia kodamae*, *Pichia membranaefaciens*, *Pichia opuntiae*, *Pichia thermotolerans*, *Pichia salictaria*, *Pichia quercuum*, *Pichia pijperi*, *Pichia stipitis*, *Pichia methanolica*, *Pichia angusta*, *Kluyveromyces lactis*, *Candida albicans*, and *Yarrowia lipolytica*.

In some embodiments on the invention, the host cell is an algal such as, *Chlamydomonas* (e.g., *C. Reinhardtii*) and *Phormidium* (*P.* sp. ATCC29409).

In other embodiments, the host cell is a prokaryotic cell. Suitable prokaryotic cells include gram positive, gram negative and gram-variable bacterial cells. The host cell may be a species of, but not limited to *Agrobacterium*, *Acinetobacter*, *Azobacter*, *Bacillus*, *Bifidobacterium*, *Buchnera*, *Geobacillus*, *Campylobacter*, *Clostridium*, *Corynebacterium*, *Escherichia*, *Enterococcus*, *Erwinia*, *Flavobacterium*, *Lactobacillus*, *Lactococcus*, *Pantoea*, *Pseudomonas*, *Staphylococcus*, *Salmonella*, *Streptococcus*, *Streptomyces*, and *Zymomonas*.

In some embodiments, the bacterial host cell is of the *Bacillus* species, e.g., *B. thuringiensis*, *B. anthracia*, *B. megaterium*, *B. subtilis*, *B. lentus*, *B. circulans*, *B. pumilus*, *B. lautus*, *B. coagulans*, *B. brevis*, *B. firmus*, *B. alkaophius*, *B. licheniformis*, *B. clausii*, *B. stearothermophilus*, *B. halodurans* and *B. amyloliquefaciens*. In particular embodiments, the host cell will be an industrial *Bacillus* strain including but not limited to *B. subtilis*, *B. pumilus*, *B. licheniformis*, *B. megaterium*, *B. clausii*, *B. stearothermophilus* and *B. amyloliquefaciens*. Some preferred embodiments of a *Bacillus* host cell include *B. subtilis*, *B. licheniformis*, *B. megaterium*, *B. stearothermophilus* and *B. amyloliquefaciens*. In some embodiments the bacterial host cell is of the *Streptomyces* species, e.g., *S. ambofaciens*, *S. achromogenes*, *S. avermitilis*, *S. coelicolor*, *S. aureofaciens*, *S. aureus*, *S. fungicidicus*, *S. griseus*, and *S. lividans*.

Strains that may be used in the practice of the invention including both prokaryotic and eukaryotic strains, are readily accessible to the public from a number of culture collections such as American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Introduction of a vector or DNA construct into a host cell can be achieved by calcium phosphate transfection, DEAE-Dextran mediated transfection, electroporation, or other common techniques as known in the art (See Davis et al., 1986, *Basic Methods in Molecular Biology*, which is incorporated herein by reference).

The engineered host cells can be cultured in conventional nutrient media modified as appropriate for activating promoters, selecting transformants, or amplifying the cellulase polynucleotide. Culture conditions, such as temperature, pH and the like, are those previously used with the host cell selected for expression, and will be apparent to those skilled in the art. As noted, many references are available for the culture and production of many cells, including cells of bacterial and fungal origin. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* (1998) from Sigma-Aldrich, Inc (St Louis, Mo.) ("Sigma-LSRCCC") and, for example, *The Plant Culture Catalogue* and supplement (1997) also from Sigma-Aldrich, Inc (St Louis, Mo.) ("Sigma-PCCS"), all of which are incorporated herein by reference.

Cells expressing the cellulase polypeptides of the invention are grown under batch or continuous fermentations conditions. Classical batch fermentation is a closed system, wherein the compositions of the medium is set at the beginning of the fermentation and is not subject to artificial alternations during the fermentation. A variation of the batch system is a fed-batch fermentation which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, the multi-cellulase enzyme composition comprises the microorganism that produced the enzyme components or comprises a crude fermentation product of the microorganisms. A crude fermentation product means a fermentation broth which has been separated from the microorganism cells or biomass. In some cases, the enzyme in the broth can be optionally concentrated, partially purified or purified and/or dried.

In some embodiments, the invention provides a multi-cellulase enzyme composition produced by culturing one or more host cell strains in a culture medium wherein the one or more host cells have been transformed with a) a nucleotide sequence encoding the an amino acid sequence having at least 95% (at least 96%, at least 97%, at least 98%, at least 99% and even 100%) sequence identity to SEQ ID NO:2, b) a nucleotide sequence encoding an amino acid sequence having at least 95% (at least 96%, at least 97%, at least 98%, at least 99% and even 100%) sequence identity to SEQ ID NO:4 or SEQ ID NO: 6, and c) a nucleotide sequence encoding an amino acid sequence having at least 95% (at least 96%, at least 97%, at least 98%, at least 99% and even 100%) sequence identity to SEQ ID NO: 8 or SEQ ID NO:10 under conditions which will allow the growth of the host cell strains and expression and production of the cellulase enzymes from the transformed strains. In some embodiments, the host cell strain will be a *Bacillus* strain. In some embodiments, the enzyme composition will comprise a culture comprising *Bacillus* strains transformed with one or more of the cellulase enzymes encompassed by the invention. In some embodiments, the host strain will be a filamentous fungal strain.

The cellulase polypeptides whether produced in a single microbial strain or produced in different microbial strains may be separated (e.g., recovered or isolated) and optionally purified by any of a number of methods known in the art. For example, the polypeptide may be isolated from the nutrient medium by conventional procedures including, but not limited to, centrifugation, filtration, extraction, spray-drying, evaporation, chromatography (e.g., ion exchange, affinity, hydrophobic interaction, chromatofocusing, and size exclusion), or precipitation. Protein refolding steps can be used, as desired, in completing the configuration of the mature protein. Finally, high performance liquid chromatography (HPLC) can be employed in the final purification steps. A variety of purification methods are well known in the art, including, for example, those set forth in Sandana (1997) *Bioseparation of Proteins*, Academic Press, Inc.; Bollag et al. (1996) *Protein Methods*, $2^{nd}$ Edition, Wiley-Liss, NY; Walker (1996) *The Protein Protocols Handbook* Humana Press, NJ; Harris and Angal (1990) *Protein Purification Applications: A Practical Approach*, IRL Press at Oxford, Oxford, England; Harris and Angal *Protein Purification Methods: A Practical Approach*, IRL Press at Oxford, Oxford, England; Scopes (1993) *Protein Purification: Principles and Practice* $3^{rd}$ Edition, Springer Verlag, NY; Janson and Ryden (1998) *Protein Purification: Principles, High Resolution Methods and Applications, Second Edition*, Wiley-VCH, NY; and Walker (1998) *Protein Protocols on CD-ROM*, Humana Press, NJ, all of which are incorporated herein by reference.

Methods are well known in the art to determine the activity of different cellulases. Some examples of assays include but are not limited to the assays described hereinbelow. To determine CBH activity, one skilled in the art can use a cellulose assay which uses Avicel® (Sigma) as a substrate. For example, in a total volume of 150 μL, 60 μL clear media supernatant containing a CBH enzyme may be added to 200 g/L Avicel in 100-250 mM sodium acetate buffer (pH 3-6). The reaction may be incubated at 50-70° C. for 24 hours and carried out using HTP format in deep well plates. Biotransformations can be quenched with 50% acetonitrile. Each plate is then centrifuged, and the supernatant collected and filtered. Conversion of Avicel to soluble sugar oligomers may be measured using an Agilent HPLC 1200 equipped with HPX-87H Ion exclusion column (300 mm×7.8 mm) with 5 mM $H_2SO_4$ at a flow rate of 0.6 ml/min at 65° C.

To determine EG activity, one skilled in the art can use the colorimetric para-nitrophenyl-β-D-cellobioside (pNPC) assay. For example, in a total volume of 150 μL, 50 μL clear media supernatant containing EG enzyme may be added to 5 mM pNPC (Sigma) solution in 25 mM sodium acetate buffer, pH 4-5. The reaction may be incubated at pH 5, 50° C. or pH 4, 70° C. for 24 hrs. The reaction mixture may be quenched with 1M sodium carbonate pH 11 solution. EG activity is then calculated by determining the conversion of pNPC to p-nitrophenyl measured at 405 nm. EG activity may also be determined using Avicel (Sigma) as substrate. For example, in a total volume of 150 μL, 75 μL clear media supernatant containing EG enzyme is added to 200 g/L Avicel in 300 mM sodium acetate buffer (pH 4-5). The reaction may be incubated at 50-70° C. for 24 hours. Biotransformations are quenched with 150 μL of 10 mM sulfuric acid. Conversion of Avicel to soluble sugar oligomers can be measured using an Agilent HPLC 1200 equipped with HPX-87H Ion exclusion column with water as eluent at a flow rate of 1.0 mL/min at 80° C.

To determine BG activity, one skilled in the art may use the colorimetric para-nitrophenyl-β-D glucopyranoside (pNPG) assay. For example, in a total volume of 100 μL, 20 μL clear media supernatant containing BG enzyme may be added to 4 mM pNPG (Sigma-Aldrich) solution in 50 mM sodium phosphate buffer at pH6.5. The reaction may be incubated at pH 6.5, 45° C. for 1 hour and then quenched with 100 μL of 1M sodium carbonate pH 11 solution. To calculate BG activity, the conversion of pNPG to p-nitrophenol is measured at 405 nm. Reference is also made to Brevis et al., (1997) *Appl. Environ. Microbiol.* 63:3902. In addition, BG activity can be measured using a cellobiose assay using cellobiose as a substrate. In a total volume of 100 μL, 25 μL clear media supernatant containing BG enzyme is added to 10 g/L cellobiose (Fluka Cat. No. 22150, Sigma-Aldrich, Inc., St. Louis, Mo.) in 100 mM sodium phosphate buffer (pH 6-7) or sodium acetate buffer (pH 5-5.5). The reaction is incubated at 45-70° C. for an appropriate time (25 minutes to overnight depending on the enzyme concentration). Glucose production is determined using an enzymatic glucose assay (K-GLUC, Megazyme, Ireland). The glucose oxidase enzyme in the reagent reacts with any glucose present in the sample and produces hydrogen peroxide which reacts with the 4-aminoantipyrine to produce a quinoneimine dye in quantities proportionate with the amount of glucose present and can be measured spectrophotometrically at 510 nm.

IV. Methods of Using the Multi-Cellulase Enzyme Compositions

In some embodiments, the present invention provides several methods of hydrolyzing a cellulose substrate to a fermentable sugar comprising a) contacting an aqueous slurry comprising a cellulose substrate with a multi-cellulase enzyme composition comprising a CBH enzyme comprising at least 90% sequence identity to SEQ ID NO: 2, an EG enzyme comprising at least 90% sequence identity to SEQ ID NO: 4 or SEQ ID NO:6 and a BG enzyme comprising at least 90% sequence identity to SEQ ID NO:8 or SEQ ID NO:10 and b) hydrolyzing the substrate under sufficient conditions to produce a hydrolysis product comprising fermentable sugars comprising glucose. In some embodiments, the cellulases which comprise the multi-enzyme composition will include any combination of the cellulases as described above in section II for CBH, EG and BG. In some embodiments the cellulases comprising the multi-enzyme composition of the invention will have at least 95% sequence identity to SEQ ID NOs: 2, 4, 6, 8, and/or 10. In some embodiments, the cellulases which comprise the enzyme compositions will have at least 97% sequence identity to SEQ ID NOs: 2, 4, 6, 8, and/or 10. In some embodiments, as described above, the CBH, EG and BG cellulase components of the multi-enzyme composition will include at least 1, at least 2, at least 3, at least 4, at least 5, at least 6, at least 7 at least 8 or more amino acid substitutions as compared to SEQ ID NO: 2, 4, 6, 8, and/or 10.

In some embodiments, the biomass includes cellulosic substrates. A cellulosic substrate may be biomass such as agricultural biomass, for example grasses (e.g., corn, wheat, rice, barley, rye, oat, rice and switch grass), wheat straw, oat straw, corn stover, soybeans, soybean stover, herbaceous crops, sugar cane bagasse, corn kernels, corn fiber, by-products from wet and dry milling of grains such as corn, wheat and barley. Agricultural biomass includes branches, canes, corn and corn husks, energy crops (e.g., switchgrass, miscanthus, and bermudagrass), fruits, flowers, grains, leaves, bark, roots, sugar beet pulp, hulls, seed coats from sunflowers and canola, wood, wood pulp, paper pulp, paper and pulp processing waste, fruit or vegetable pulp distillers grains or distiller's dried grains (DDGs) with soluble material (DDGSs), hard and softwoods (e.g., popular and spruce) and any mixture of the above. In some embodiments, the biomass is obtained from wheat straw, corn stover, corn cobs, oat straw, barley straw, rice straw, miscanthus, switch grass, sugar cane bagasse, soybean stover or combinations thereof.

The multi-cellulase enzyme composition may be added to the aqueous slurry of the biomass at any point prior to the introduction of the slurry into a reactor vessel or may be added directly to the reactor vessel. The reactor vessel is a vessel used to carry out a partial or complete hydrolysis of the cellulosic substrate. Those having ordinary skill in the art will appreciate that the reaction times for converting a particular biomass substrate to a fermentable sugar may vary but the optimal reaction time can be readily determined. Exemplary reaction times may be in the range of from about 4 to 260 hours, from about 5 to about 240, from about 10 to about 200 hours, from about 15 to about 180 hrs and from about 15 to about 150 hrs. For example, the incubation or contacting time may be at least 5 hr, at least 10 hrs, at least 20 hrs, at least 25 hrs, at least 30 hrs, at least 40 hr, at least 50 hrs, at least 100 hrs and the like.

In addition to the hydrolysis time described above, conditions suitable for converting a biomass substrate to a fermentable sugar that employs a multi-cellulase enzyme composition of the present invention is a pH in a range from about pH 3.0 to about 10.0, about pH 3.5 to pH 9.5, about pH 3.5 to about 8.5, about pH 4.0 to about 7.5, about pH 4.0 to about 7.0, about pH 4.0 to about 6.5, about pH 4.5 to about 6.5, about pH 5.0 to about 6.5, and about pH 5.5 to about 6.5.

Suitable temperatures for the contacting and hydrolysis is a temperature in the range of about 20° C. to about 100° C., about 25° C. to about 95° C., about 30° C. to about 90° C., about 30° C. to about 80° C., about 40° C. to about 80° C., about 45° C. to about 75° C., and about 50° C. to about 70° C. Also the biomass may be reacted with the compositions at a temperature about 25° C., at about 30° C., at about 35° C., at about 40° C., at about 45° C., at about 50° C., at about 55° C., at about 60° C., at about 65° C., at about 70° C., at about 75° C., at about 80° C., at about 85° C., at about 90° C., at about 95° C. and at about 100° C.

The amount of fermentable sugars produced under the above conditions during the hydrolysis step will vary depending on the biomass substrate. In some embodiments, at least 5% of the total available fermentable sugars are released during the hydrolysis. In other embodiments, at least 8%, at least 10%, at least 12%, at least 15%, at least 20%, at least 22%, at least 25%, and at least 30% of the fermentable sugars are released during the hydrolysis. In some embodiments, during the hydrolysis step at least 60%, at least 65%, at least 70%, at least 75%, at least 80%, at least 85%, at least 90%, at least 92%, at least 95%, at least 96%, at least 98%, at least 99% and in some embodiments also 100% of the cellulose is converted to glucose In some embodiments, the present invention provides a method of hydrolyzing a cellulosic substrate to a fermentable sugar comprising a) pretreating a cellulosic substrate, b) contacting the pretreated substrate with a multi-cellulase enzyme composition encompassed by the invention such as comprising a CBH enzyme comprising at least 95% (also at least 97%, at least 99% and/or even 100%) sequence identity to SEQ ID NO: 2, an EG enzyme comprising at least 95% (also at least 97% at least 99% and/or even 100%) sequence identity to SEQ ID NO: 4 or SEQ ID NO:6, and a BG enzyme comprising at least 95% (also at least 97%, at least 99% and/or even 100%) sequence identity to SEQ ID NO:8 or SEQ ID NO: 10 and c) hydrolyzing the pretreated substrate under sufficient conditions to produce a hydrolysis product comprising fermentable sugars comprising glucose.

Pretreatment may be achieved by using methods known in the art such as chemical, physical and biological pretreatments. Conventional pretreatment methods include, but are not limited to steam pretreatment (with or without explosion), dilute acid pretreatment, wet oxidation pretreatment, hot water pretreatment, ammonia fiber pretreatment (e.g., AFEX); mechanical and physical pretreatment as well as biological pretreatment. Pretreatment is preferably carried out prior to hydrolysis with the cellulase enzymes. Non-limiting examples of these chemical pretreatment methods may be found for example in USP Application No. 20020164730 and Sassner et al., 2006, *Enzyme Microb. Technol.* 39:756-762 for steam pretreatment; Duff and Murray, 1996, *Bioresource Technol.* 855:1-33 for dilute acid pretreatment; and Gollapalli et al., 2002, *Appl. Biochem. Biotechnol.* 98:23-35 and Teymouri et al., 2005, *Bioresource Technol.* 96:2014-2018 for AFEX. Mechanical and physical pretreatments include but are not limited to various types of milling such as but not limited to wet milling or dry milling. In addition, combinations of pretreatment may be used. Additional useful references related to dilute acid pretreatment include: Schell et al. (2003) *Appl. Biochem and Biotech.*, Vol. 105:69-85; Knappert D, et al., (1980), *Biotechnol Bioeng* 22:1449-1463; Torget, R., et al., (1991), *Appl. Biochem. Biotechnol.*, 28/29:75-86; Esteghlalian, A., et al., (1997), *Bioresour. Technol.* 59:129-136; and Chen, R. et al., (1996), *Appl. Biochem.Biotechnol.* 57/58: 133-146.

In additional embodiments, the method according to the invention comprises recovering or isolating the fermentable sugars. Methods for recovering fermentable sugars from culture broth are known in the art and include but are not limited to washing, pressure, chromatography extraction, crystallization, membrane separation, osmosis, distillation, and filtration.

The present invention also provides a method for fermenting the fermentable sugars with at least one fermenting microorganism to produce end-products and optionally recovering the end-products. The fermenting microorganism will be one that can metabolize C6 and/or C5 sugars. In some embodiments, the fermenting microorganism will be a wildtype organism and in other embodiments, the fermenting microorganism will be a recombinant microorganism. In some embodiments, the fermenting microorganism will be a yeast (e.g., *Saccharomyces* sp., such as, for example, *S. cerevisiae*, *Candida* sp., *Pichia* sp. *Kluyveromyces* sp., and/or *Yarrowia* sp.). In other embodiments, the fermenting microorganism will be a bacterial strain such as *Zymomonas* sp., *Clostridium* sp. *Streptomyces* sp., or *E. coli*. The fermentation step may be carried out in a simultaneous saccharification and fermentation (SSF) process or in a sequential saccharification and fermentation process.

Depending on the fermenting microorganism, various end-products may be produced. In one embodiment, the end-product includes alcohols (such as, but not limited to ethanol and butanol). In other embodiments, the end-products may include metabolic products such as organic acids, amino acids, vitamins, pharmaceuticals, animal feed supplements, specialty chemicals, hydrocarbons and other organic compounds. In some preferred embodiments the end-product includes, biofuels (e.g., ethanol and butanol), lactic acid, succinic acid, ascorbic acid, lysine, glycine, glycerol, diols (1,3, propanediol) and animal feed supplements.

In one preferred embodiment, the method of the invention comprises a method of hydrolyzing a cellulosic substrate to obtain an alcohol comprising a) pretreating a cellulosic substrate, b) contacting the pretreated substrate with a multi-cellulase enzyme composition encompassed by the invention such as comprising a CBH enzyme comprising at least 95% (also at least 97%, at least 99% and/or even 100%) sequence identity to SEQ ID NO:2, an EG enzyme comprising at least 95% (also at least 97%, at least 99% and/or even 100%) sequence identity to SEQ ID NO:4 and/or SEQ ID NO: 6, and a BG enzyme comprising at least 95% (also at least 97%, at least 99% and/or even 100%) sequence identity to SEQ ID NO:8 and/or SEQ ID NO:10, c) hydrolyzing the pretreated substrate under sufficient conditions to produce a hydrolysis product comprising fermentable sugars comprising glucose, d) fermenting the fermentable sugars with a fermenting microorganism under sufficient conditions to produce an alcohol, and recovering the alcohol. In some preferred embodiments, the alcohol is ethanol, the pretreated substrate is obtained from bagasse, wheat and/or corn biomass and the fermenting microorganism is a yeast and particularly a strain of *Saccharomyces* and/or *Yarrowia*.

The foregoing and other aspects of the invention may be better understood in connection with the following non-limiting examples.

V. Examples

Example 1

CBH, EG and BG Enzymes

The following enzymes were used in the examples below—a) CBH enzyme having the amino acid sequence disclosed as SEQ ID NO: 2; b) EG-1 enzyme having the amino acid sequence disclosed as SEQ ID NO: 4 and EG-2 enzyme having the amino acid sequence disclosed as SEQ ID NO: 6; and c) BG-1 enzyme having the amino acid sequence disclosed as SEQ ID NO: 8 and BG-2 having the amino acid sequence disclosed as SEQ ID NO:10. Each of these enzymes are evolved variants, which originated from different wild-type bacterial genes as further described in co-pending applications PCT/US10/47324 filed Aug. 31, 2010; U.S. Ser. No. 12/751,985 filed Mar. 31, 2010; and U.S. Ser. No. 12/816,989 filed Jun. 16, 2010. Each of these references is incorporated by reference herein in their entirety. In general, each cellulase enzyme (e.g., the enzyme comprising SEQ ID NO:2, SEQ ID NO:4, SEQ ID NO:6, SEQ ID NO:8 or SEQ ID NO:10) was concentrated approximately 10-15 fold from the clarified fermentation broth using a ultra-filtration membrane with a molecular weight cut off of 10 kDa. The concentrate was stored at 4° C. until further use and protein concentrations were determined by an Agilent 2100 Bio-analyzer.

Example 2

Mixture Experiments on Avicel®

The cellulase enzymes were tested at different ratios to determine their optimal ratio in the multi-cellulase mixture. The mixture experiments were designed using Design Expert 7 (Stat-ease Inc, MN). Prepared mixtures were evaluated on 200 g/L Avicel® (Sigma-Aldrich®) prepared in a 250 mM acetate buffer. Total protein load was 1 g/L. The mixtures were evaluated at (a) pH 5.5 and 55° C. and (b) pH 5.0 and 65° C. Experiments were carried out in high throughput (HTP) format in deep well plates. After 48 hours incubation, reactions were quenched with 50% acetonitrile. Each plate was centrifuged and the supernatant was collected and filtered. Conversion of Avicel® to soluble sugar oligomers (cellobiose and glucose) was measured using an Agilent HPLC 1200 equipped with a HPX-87H ion exclusion column, with 5 mM $H_2SO_4$ at a flow rate of 0.6 ml/min at 65° C. The retention times of the cellobiose and glucose were 7.5 and 9.1 minutes, respectively. A representative data set is shown in Tables 1 and 2. All experiments were conducted in duplicates and the values are averaged over two measurements.

TABLE 1

Cellobiose and glucose yields with CBH, EG-1 and BG-1 at pH 5.5, 55° C. for 48 hrs.

| EG-1 g/L | BG-1 g/L | CBH g/L | Cellobiose g/L | Glucose g/L | Cellobiose + Glucose g/L |
|---|---|---|---|---|---|
| 1 | 0 | 0 | 2.5 | 5 | 7.5 |
| 0 | 0 | 1 | 8.5 | 0.2 | 9 |
| 0.167 | 0.167 | 0.666 | 0 | 22 | 22 |
| 0.33 | 0.33 | 0.33 | 0 | 22 | 22 |

TABLE 2

Cellobiose and glucose yields with CBH, EG-2 and BG-1 at pH 5.0, 65° C. for 48 hrs.

| EG-2 g/L | BG-1 g/L | CBH g/L | Cellobiose g/L | Glucose g/L | Cellobiose + Glucose g/L |
|---|---|---|---|---|---|
| 0.2 | 0.3 | 0.5 | 12.7 | 5.2 | 17.9 |
| 0.5 | 0.8 | 0.87 | 18.5 | 2.7 | 21.2 |

Example 3

Synergy Experiments on Avicel®

Synergy experiments were designed in Design Expert (Stat-ease Inc, MN) using factorial design. The multi-cellulase mixtures were evaluated on 200 g/L Avicel (Sigma-Aldrich®) prepared in 250 mM acetate buffer, at pH 5.5 and 55° C. Experiments were carried out in high throughput (HTP) format in deep well plates. A range of enzyme concentrations were evaluated (0.6 to 1.4 g/L). Incubation time was 48 hours and reactions were quenched with 50% acetonitrile. Each plate was centrifuged and the supernatant was collected and filtered. Conversion of Avicel to soluble sugar oligomers (cellobiose and glucose) was measured using an Agilent HPLC 1200 equipped with HPX-87H ion exclusion column, with 5 mM $H_2SO_4$ at a flow rate of 0.6 ml/min at 65° C. The retention times of the cellobiose and glucose were 7.5 and 9.1 minutes respectively. A representative data set is shown in Table 3. All experiments were conducted in duplicates and the values are averaged over two measurements.

TABLE 3

Cellobiose and glucose yield with CBH, EG-2 and BG-1 at pH 5.5, 55° C. for 48 hr.

| EG-1 g/L | BG-1 g/L | CBH g/L | Cellobiose g/L | Glucose g/L | Cellobiose + Glucose, g/L | Degree of Synergy (DS) |
|---|---|---|---|---|---|---|
| 0.6 | 0 | 0 | 2.4 | 6.6 | 9.0 | 1 |
| 0 | 0 | 0.9 | 13.5 | 0.3 | 13.8 | 1 |
| 0 | 1.4 | 0 | 0 | 2.75 | 2.75 | 1 |
| 0.6 | 0 | 0.9 | 12.3 | 6.3 | 18.6 | 0.82 |
| 0.6 | 1.4 | 0 | 0 | 11.8 | 11.8 | 1 |
| 0 | 1.4 | 0.9 | 1.1 | 36.2 | 37.3 | 2.25 |
| 0.6 | 1.4 | 0.9 | 0.8 | 55.8 | 56.6 | 2.22 |

Example 4

Activity of Cellulase Mixture on Pretreated Bagasse

Pretreated bagasse was contacted with EG-2, CBH and BG-2 enzymes and mixtures thereof and a total substrate load of 50 g/L was evaluated. Each enzyme was used in the range of 0.5 to 1.0 g/L and hydrolysis was conducted at pH 5.5 and 55° C. for 72 hours in the presence of 250 mM acetate buffer. Reactions were quenched with 50% acetonitrile. Each HTP reaction plate was centrifuged and the supernatant (150 uL) was collected and filtered. Conversion of biomass to soluble sugar oligmers (cellobiose+glucose) was measured using an Agilent HPLC 1200 equipped with HPX-87H ion exclusion column with 5 mM $H_2SO_4$ at a flow rate of 0.6 ml/min at 65° C. The retention times of cellobiose and glucose was 7.5 and 9.1 minutes respectively. The DS with the multi-cellulase mixture was observed to be between 1.0 and 1.8. A representative data set is shown in Table 4. All experiments were conducted in duplicates and the values are averaged over two measurements.

TABLE 4

Cellobiose and glucose yield with CBH, EG-2 and BG-2 at pH 5.0, 65° C. for 72 hrs.

| EG-2 g/L | BG-2 g/L | CBH g/L | Cellobiose g/L | Glucose g/L | Cellobiose + Glucose, g/L | Degree of Synergy (DS) |
|---|---|---|---|---|---|---|
| 0.5 | 0 | 0 | 2.5 | 2.0 | 4.5 | 1 |
| 0 | 0 | 1 | 2.3 | 0.1 | 2.4 | 1 |
| 0 | 0.6 | 0 | 0 | 0.6 | 0.6 | 1 |
| 0.5 | 0 | 1 | 8.0 | 1.6 | 9.6 | 1.4 |
| 0.5 | 0.6 | 0 | 0 | 5.6 | 5.6 | 1.09 |
| 0 | 0.6 | 1 | 0 | 3.0 | 3.0 | 1 |
| 0.5 | 0.6 | 1 | 0 | 13.7 | 13.7 | 1.82 |

Example 5

Mixture Experiments on Pretreated Corn Stover

Pretreated corn stover was obtained from NREL and was exposed to a cellulase mixture of CBH, EG-2 and BG-2. Substrate loadings of 30 g/L were prepared in 250 mM acetate buffer, pH 5.5. Enzymes were used in the range of 0.75-1.8 g/L and each reaction was conducted at 55° C. for 72 hours. Reactions were quenched with 50% acetonitrile. As described above, each plate was centrifuged and the supernatant (150 uL) was collected and filtered. Conversion of biomass to soluble sugar oligomers (cellobiose+glucose) was measured using an Agilent HPLC 1200 equipped with HPX-87H ion exclusion column with 5 mM $H_2SO_4$ at a flow rate of 0.6 ml/min at 65° C. The retention times of the cellobiose and glucose were 7.5 and 9.1 minutes respectively. A representative data set is shown below in Table 5.

TABLE 5

Cellobiose and glucose yield with CBH, EG-2 and BG-2 on pretreated corn stover.

| EG-2 g/L | BG-2 g/L | CBH g/L | Cellobiose g/L | Glucose g/L | Cellobiose + Glucose g/L |
|---|---|---|---|---|---|
| 1.3 | 0 | 1.8 | 5.5 | 1.2 | 6.7 |
| 1.3 | 0.75 | 0 | 1.1 | 1.8 | 2.9 |
| 0 | 0.75 | 1.8 | 3.3 | 0.9 | 4.2 |
| 1.3 | 0.75 | 1.8 | 3.8 | 2.1 | 5.8 |

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modifications are intended to be within the scope of the claims appended hereto.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

It is claimed:

1. A multi-cellulase enzyme composition for the enzymatic hydrolysis of a substrate comprising cellulose, said composition comprising: a cellobiohydrolase (CBH) enzyme, an endoglucanase (EG) enzyme and a β-glucosidase (BG) enzyme, wherein the CBH enzyme comprises the amino acid sequence of SEQ ID NO:2; the EG enzyme comprises the amino acid sequence of SEQ ID NO:4 and/or the amino acid sequence of SEQ ID NO:6; and the BG enzyme comprises the amino acid sequence of SEQ ID NO:8 and/or the amino acid sequence of SEQ ID NO: 10.

2. The enzyme composition of claim 1, wherein the CBH enzyme component is present at greater than 70 wt % and less than 98 wt %, the EG enzyme component is present at greater than 15 wt % and less than 45 wt %, and the BG enzyme component is present at greater than or equal to 5 wt % and less than 45 wt %.

3. The enzyme composition of claim 1, wherein the CBH, EG, and BG enzyme components are each produced from a different host cell.

4. The enzyme composition of claim 1 further comprising accessory enzymes.

5. The enzyme composition of claim 4, wherein the accessory enzymes include additional cellulases, hemicellulases and/or esterases.

6. A method of hydrolyzing a cellulose substrate to a fermentable sugar comprising contacting an aqueous slurry comprising a substrate comprising cellulose with the multi-cellulase enzyme composition of claim 1, and hydrolyzing the substrate under conditions sufficient to produce a hydrolysis product comprising fermentable sugars comprising glucose.

7. The method according to claim 6, wherein the aqueous slurry is obtained from agricultural residue or grasses.

8. The method according to claim 7, wherein the agricultural residue is from corn stover, corn fiber, wheat straw, oat straw, barley straw, rice straw, miscanthus, switch grass, sugar cane, bagasse, soybean stover, sugar beet pulp or combinations thereof.

9. The method according to claim 6 further comprising pretreating the substrate comprising cellulose.

10. The method according to claim 9, wherein at least 70% of the pretreated substrate is converted to glucose.

11. The method according to claim 6, wherein the method is conducted at a temperature of 45 to 75° C.

12. The method according to claim 6, wherein the method is conducted at a pH of 4.0 to 6.5.

13. The method according to claim 6 further comprising fermenting the fermentable sugars with a fermenting microorganism under conditions sufficient to obtain an end-product.

14. The method according to claim 13, wherein the fermenting microorganism is a yeast.

15. The method according to claim 13, wherein the end-product is an alcohol.

16. The method according to claim 15, wherein the alcohol is ethanol.

17. The method according to claim 13, wherein the end-product is an organic acid, amino acid, hydrocarbon or diol.

* * * * *

SEQUENCE LISTING

<160> NUMBER OF SEQ ID NOS: 10

<210> SEQ ID NO 1
<211> LENGTH: 1275
<212> TYPE: DNA
<213> ORGANISM: Artificial
<220> FEATURE:
<223> OTHER INFORMATION: Synthetic DNA construct

<400> SEQUENCE: 1

```
atggggcctg ctgcacctac tgcacgtgtg dataatcctt atgtaggcgc gacaatgtac      60
gtaaatccag aatggtcagc tcttgctgct tcggaaccag gtggtgatcg tgttgcagat     120
caacctacgg ctgtttggtt agatcgtatt gcaactattg aaggtgttga tggaaaaatg     180
ggattacgag aacatcttga tgaagcgtta caacaaaaag gaagcggaga acttgtggta     240
cagttagtaa tttatgattt acctggtcgt gattgcgcgg ctcttgctag taatggtgaa     300
ttaggtcctg atgaattaga tcgatataaa agcgaatata ttgatccgat tgcagacatt     360
ttatcggatt ccaaatatga aggacttcgt attgttacgg ttattgaacc agacagctta     420
cctaatttag taacaaacgc aggtggtaca gatacaacga cagaagcatg tactactatg     480
aaagcaaacg gtaattatga aaaggggta tcgtatgcgc tttctaaatt aggtgcaatt     540
ccgaacgtat acaactatat tgatgctgct catcatggat ggttaggatg gacacaaat     600
tttgggccat ccgtacagga attttataaa gtggcaacat caaatggcgc atccgttgat     660
gatgtggcgg gatttgcagt caatacagct aattattcag caactgtaga accttatttt     720
acggtttcag atacggtgaa tgggcagacg gtacgtcaat ctaaatgggt tgactggaat     780
caatacgtag atgaacaaag ttatgcgcag gctttacgaa acgaagctgt cgccgctgga     840
tttaatagcg atattggtgt gattattgat acatcccgaa atggatgggg tggtccagat     900
cgcccttcag ggcctggccc tcaaacttcc gtagatgctt atgtagatgg atcacgaatt     960
gatcgtcgcg ttcatgtagg aaattggtgt aatcagtctg gagcaggctt aggtgaaaga    1020
ccaacagcag caccagctag cgggattgat gcatatacat ggattaaacc gccgggcgaa    1080
tctgatggaa attcagctcc ggttgataat gacgaaggaa aaggatttga ccgtatgtgt    1140
gatcctagct accagggaaa cgctcgcaat ggctacaatc cttcaggagc gttacctgat    1200
gcaccattaa gtggacaatg gttttcggca caatttcgtg aattaatgca aaatgcatat    1260
cctccattat cttga                                                     1275
```

<210> SEQ ID NO 2
<211> LENGTH: 424
<212> TYPE: PRT
<213> ORGANISM: Artificial
<220> FEATURE:
<223> OTHER INFORMATION: Synthetic polypeptide

<400> SEQUENCE: 2

Met Gly Pro Ala Ala Pro Thr Ala Arg Val Asp Asn Pro Tyr Val Gly
1               5                   10                  15

Ala Thr Met Tyr Val Asn Pro Glu Trp Ser Ala Leu Ala Ala Ser Glu
            20                  25                  30

Pro Gly Gly Asp Arg Val Ala Asp Gln Pro Thr Ala Val Trp Leu Asp
        35                  40                  45

Arg Ile Ala Thr Ile Glu Gly Val Asp Gly Lys Met Gly Leu Arg Glu
    50                  55                  60

His Leu Asp Glu Ala Leu Gln Gln Lys Gly Ser Gly Glu Leu Val Val

|     |     |     |     |     | 65  |     |     |     |     | 70  |     |     |     |     | 75  |     |     |     |     | 80  |
|-----|-----|-----|-----|-----|-----|-----|-----|-----|-----|-----|-----|-----|-----|-----|-----|-----|-----|-----|-----|-----|

Gln Leu Val Ile Tyr Asp Leu Pro Gly Arg Asp Cys Ala Ala Leu Ala
            85                  90                  95

Ser Asn Gly Glu Leu Gly Pro Asp Glu Leu Asp Arg Tyr Lys Ser Glu
            100                 105                 110

Tyr Ile Asp Pro Ile Ala Asp Ile Leu Ser Asp Ser Lys Tyr Glu Gly
            115                 120                 125

Leu Arg Ile Val Thr Val Ile Glu Pro Asp Ser Leu Pro Asn Leu Val
130                 135                 140

Thr Asn Ala Gly Gly Thr Asp Thr Thr Thr Glu Ala Cys Thr Thr Met
145                 150                 155                 160

Lys Ala Asn Gly Asn Tyr Glu Lys Gly Val Ser Tyr Ala Leu Ser Lys
            165                 170                 175

Leu Gly Ala Ile Pro Asn Val Tyr Asn Tyr Ile Asp Ala Ala His His
            180                 185                 190

Gly Trp Leu Gly Trp Asp Thr Asn Phe Gly Pro Ser Val Gln Glu Phe
            195                 200                 205

Tyr Lys Val Ala Thr Ser Asn Gly Ala Ser Val Asp Asp Val Ala Gly
            210                 215                 220

Phe Ala Val Asn Thr Ala Asn Tyr Ser Ala Thr Val Glu Pro Tyr Phe
225                 230                 235                 240

Thr Val Ser Asp Thr Val Asn Gly Gln Thr Val Arg Gln Ser Lys Trp
            245                 250                 255

Val Asp Trp Asn Gln Tyr Val Asp Glu Gln Ser Tyr Ala Gln Ala Leu
            260                 265                 270

Arg Asn Glu Ala Val Ala Ala Gly Phe Asn Ser Asp Ile Gly Val Ile
            275                 280                 285

Ile Asp Thr Ser Arg Asn Gly Trp Gly Gly Pro Asp Arg Pro Ser Gly
            290                 295                 300

Pro Gly Pro Gln Thr Ser Val Asp Ala Tyr Val Asp Gly Ser Arg Ile
305                 310                 315                 320

Asp Arg Arg Val His Val Gly Asn Trp Cys Asn Gln Ser Gly Ala Gly
            325                 330                 335

Leu Gly Glu Arg Pro Thr Ala Ala Pro Ala Ser Gly Ile Asp Ala Tyr
            340                 345                 350

Thr Trp Ile Lys Pro Pro Gly Glu Ser Asp Gly Asn Ser Ala Pro Val
            355                 360                 365

Asp Asn Asp Glu Gly Lys Gly Phe Asp Arg Met Cys Asp Pro Ser Tyr
            370                 375                 380

Gln Gly Asn Ala Arg Asn Gly Tyr Asn Pro Ser Gly Ala Leu Pro Asp
385                 390                 395                 400

Ala Pro Leu Ser Gly Gln Trp Phe Ser Ala Gln Phe Arg Glu Leu Met
            405                 410                 415

Gln Asn Ala Tyr Pro Pro Leu Ser
            420

<210> SEQ ID NO 3
<211> LENGTH: 1029
<212> TYPE: DNA
<213> ORGANISM: Artificial
<220> FEATURE:
<223> OTHER INFORMATION: Synthetic DNA construct

<400> SEQUENCE: 3
gatactagta tggatacttc tatttgtgaa ccatttggat ctactacaat ccaaggacgc    60

```
tatgtagtac agaataatcg ttggggcaca agtgaaccgc aatgtataac agcaaccgat    120
tcaggattcc gcattaccca agcggatggt tctgtaccaa cgaatggtcc gcctaaatct    180
tatccaagtg tctataacgg atgtcattat acaaattgct ctcctgggac gccgcttcca    240
gcccaattat caacagtttc atctgctcca acatctatta gttattctta cgtgtcaaat    300
gccatgtatg atgccgcgta cgacatttgg ttagatccaa caccgcgcac agatggtgta    360
aatcgaacag aaatcatggt gtggtttaat aaagtaggca gcgtgcagcc agtaggatct    420
caagtaggta cggctacggt ggcaggccga caatggcagg tttggtcagg aaataacgga    480
tctaatgatg tgcttagttt cgtagctcca agtgccatta cttcatggtc ttttgatgta    540
atggactttg ttcgtcaagc cgttagtcgc ggattagctc aaccgtcttg gtatttgaca    600
tctgtccaag ctggatttga accgtggcag aatggcgctg gactagcagt aacttctttt    660
tcgtctacgg taaacactgg aggcggcaat ccaggagatc cgggatctcc tactgcttgc    720
aaagttgctt atgcaacgaa tgtttggcaa ggtggattta cggctgacgt aactgtaacg    780
aatacagggt cctcacctgt caatggatgg aaacttgctt ttacgttacc agcaggccaa    840
caaattactt cgtcttggtc agcaggagta tctccgtcat ctggagcagt gacagcttct    900
agccttgcat acaatgcaca aattgcaacc ggggacgtg tatcatttgg atttcaaggt    960
agttattctg gcacatttgc agcacctgca ggttttttctt taaatggggc tgcttgcaca    1020
acggcatga                                                           1029

<210> SEQ ID NO 4
<211> LENGTH: 222
<212> TYPE: PRT
<213> ORGANISM: Artificial
<220> FEATURE:
<223> OTHER INFORMATION: Synthetic polypeptide

<400> SEQUENCE: 4

Asp Thr Ser Ile Cys Glu Pro Phe Gly Ser Thr Thr Ile Gln Gly Arg
1               5                   10                  15

Tyr Val Val Gln Asn Asn Arg Trp Gly Thr Ser Glu Pro Gln Cys Ile
            20                  25                  30

Thr Ala Thr Asp Ser Gly Phe Arg Ile Thr Gln Ala Asp Gly Ser Val
        35                  40                  45

Pro Thr Asn Gly Pro Pro Lys Ser Tyr Pro Ser Val Tyr Asn Gly Cys
    50                  55                  60

His Tyr Thr Asn Cys Ser Pro Gly Thr Pro Leu Pro Ala Gln Leu Ser
65                  70                  75                  80

Thr Val Ser Ser Ala Pro Thr Ser Ile Ser Tyr Ser Tyr Val Ser Asn
                85                  90                  95

Ala Met Tyr Asp Ala Ala Tyr Asp Ile Trp Leu Asp Pro Thr Pro Arg
            100                 105                 110

Thr Asp Gly Val Asn Arg Thr Glu Ile Met Val Trp Phe Asn Lys Val
        115                 120                 125

Gly Ser Val Gln Pro Val Gly Ser Gln Val Gly Thr Ala Thr Val Ala
    130                 135                 140

Gly Arg Gln Trp Gln Val Trp Ser Gly Asn Asn Gly Ser Asn Asp Val
145                 150                 155                 160

Leu Ser Phe Val Ala Pro Ser Ala Ile Thr Ser Trp Ser Phe Asp Val
                165                 170                 175

Met Asp Phe Val Arg Gln Ala Val Ser Arg Gly Leu Ala Gln Pro Ser
```

```
                      180                 185                 190
Trp Tyr Leu Thr Ser Val Gln Ala Gly Phe Glu Pro Trp Gln Asn Gly
            195                 200                 205

Ala Gly Leu Ala Val Thr Ser Phe Ser Ser Thr Val Asn Thr
        210                 215                 220
```

<210> SEQ ID NO 5
<211> LENGTH: 1029
<212> TYPE: DNA
<213> ORGANISM: Artificial
<220> FEATURE:
<223> OTHER INFORMATION: Synthetic DNA construct

<400> SEQUENCE: 5

```
gatactagta tggatacttc tatttgtgaa ccatttggat ggactgtgat ccaaggacgc     60
tatgtagtac agaataatcg ttggggcaca agtgaaccgc aatgtataac agcaaccgat    120
tcaggattcc gcattacccg cgcggatggt tctaaaccaa cgaatggtcc gcctaaatct    180
tatccaagtg tctataacgg atgtcattat acaatttgct ctcctgggac gccgcttcca    240
gcccaaattt caaaaatttc atctgctcca acatctatta gttattctta cgtgtcaaat    300
gccgtgtatg atgccgcgta cgacatttgg ttagatccaa caccgcgcac agatggtgta    360
aatcgaacag aaatcatggt gtggtttaat aaagtaggca gcgtgcagcc agtaggatct    420
caagtaggta cggctacggt ggcaggccga caatggcagg tttggatggg aaataacgga    480
tctaatgatg tgcttagttt cgtagctcca agtgccatta cttcatggtc ttttgatgta    540
atggactttg ttcgtcaagc cgttcagcgc ggattagctc aaccgtcttg gtatttgaca    600
tctgtccaag ctggatttga accgtgggaa atggcgctg actagcagt aacttctttt    660
tcgtctacgg taaacactgg aggcggcaat ccaggagatc cgggatctcc tactgcttgc    720
aaagttgctt atgcaacgaa tgtttggcaa ggtggattta cggctgacgt aactgtaacg    780
aatacagggt cctcacctgt caatggatgg aaacttgctt ttacgttacc agcaggccaa    840
caaattactt cgtcttggtc agcaggagta tctccgtcat ctggagcagt gacagcttct    900
agccttgcat acaatgcaca aattgcaacc ggggacgtg tatcatttgg atttcaaggt    960
agttattctg gcacatttgc agcacctgca ggttttctt taaatggggc tgcttgcaca   1020
acggcatga                                                          1029
```

<210> SEQ ID NO 6
<211> LENGTH: 222
<212> TYPE: PRT
<213> ORGANISM: Artificial
<220> FEATURE:
<223> OTHER INFORMATION: Synthetic polypeptide

<400> SEQUENCE: 6

```
Asp Thr Ser Ile Cys Glu Pro Phe Gly Trp Thr Val Ile Gln Gly Arg
1               5                  10                  15

Tyr Val Val Gln Asn Asn Arg Trp Gly Thr Ser Glu Pro Gln Cys Ile
            20                  25                  30

Thr Ala Thr Asp Ser Gly Phe Arg Ile Thr Arg Ala Asp Gly Ser Lys
        35                  40                  45

Pro Thr Asn Gly Pro Pro Lys Ser Tyr Pro Ser Val Tyr Asn Gly Cys
    50                  55                  60

His Tyr Thr Ile Cys Ser Pro Gly Thr Pro Leu Pro Ala Gln Ile Ser
65                  70                  75                  80
```

```
Lys Ile Ser Ser Ala Pro Thr Ser Ile Ser Tyr Ser Tyr Val Ser Asn
             85                  90                  95

Ala Val Tyr Asp Ala Ala Tyr Asp Ile Trp Leu Asp Pro Thr Pro Arg
            100                 105                 110

Thr Asp Gly Val Asn Arg Thr Glu Ile Met Val Trp Phe Asn Lys Val
        115                 120                 125

Gly Ser Val Gln Pro Val Gly Ser Gln Val Gly Thr Ala Thr Val Ala
    130                 135                 140

Gly Arg Gln Trp Gln Val Trp Met Gly Asn Asn Gly Ser Asn Asp Val
145                 150                 155                 160

Leu Ser Phe Val Ala Pro Ser Ala Ile Thr Ser Trp Ser Phe Asp Val
                165                 170                 175

Met Asp Phe Val Arg Gln Ala Val Gln Arg Gly Leu Ala Gln Pro Ser
            180                 185                 190

Trp Tyr Leu Thr Ser Val Gln Ala Gly Phe Glu Pro Trp Glu Asn Gly
        195                 200                 205

Ala Gly Leu Ala Val Thr Ser Phe Ser Ser Thr Val Asn Thr
    210                 215                 220

<210> SEQ ID NO 7
<211> LENGTH: 1941
<212> TYPE: DNA
<213> ORGANISM: Artificial
<220> FEATURE:
<223> OTHER INFORMATION: Synthetic DNA construct

<400> SEQUENCE: 7
agtgcggcaa tcgcacagga aggagcagct ccggccgcta tgttacatcc agagaaatgg      60
cctcgacctg cgacacaacg acttattgac ccggcagttg aaaaaagagt tgatgctctg     120
ttaaaacagt tatctgttga agaaaaagta gggcaagtta tacagggtga tattgggaca     180
attacaccag aagacctgcg caaatatcca ctaggttcta ttttagccgg aggagatagc     240
ggcccgaatg gagatgatcg tgctcctcca aaggagtggc ttgatctagc tgatgctttt     300
taccgtgtaa gtttagaaaa acggccaggc ataccccga taccagtgct ttttggcatt      360
gatgcagttc atggacatgg caatatcggg tctgcgacaa ttttccctca caatattgca     420
cttggaatga cccgtgatcc agaacttcta cgaagaattg gtgaggtaac agctgaagaa     480
atggctgcca cggaattga ttggacattt gcgcctgcac tgtctgttgt gagagatgat      540
cgatggggac gaacgtatga aggcttctca gaagatccag aaattgtagc ttcttattca     600
gcagcaattg tggaaggcgt acagggtaaa tatggttcta aggattttat ggcgccgggt     660
cgcgcggtag cgtgcgcaaa gcacttctta gctgatggtg aacagatca aggacgcgat      720 cagggagatg cacgcatttc agaagacgaa ctaattcgca ttcataatgc tggataccct     780
cctgcgattg acgcaggagt gctgacagta atggcttctt tttcatcctg cagggggatt     840
aaacaccatg ccataaaca cttttaaca gatgtattaa aaggacaaat ggggtttaat       900
ggatttattg tggggattg aatgctcat gaccaagtac cgggctgtac taaatttaat       960
tgtccaacat ctcttattgc gggtttagat atgtatatgg ccgccgattc ctggaagcag    1020
ctgtacgaaa acaccttagc acaagtgaaa gatggtacta ttcctatggc acgtctagat    1080
gatgccgtaa gacgaatctt gcgagtcaag gtgttggctg cttattcga gaaacctgcg     1140 ccaaaagatc gtccgggggtt accaggcctt gaaacactag gatcacctga acatagagcc    1200
gtaggccgtg aagctgttcg aaaaagccta gttcttctta aaaatgataa aggtacccctt   1260
```

```
ccactgtcac caaaggctag agtattagtt gcaggtgacg gagcagataa tattggcaaa   1320
cagtcggggg gctggacgat tagttggcaa ggaactggaa accgtaacga tgaatttccg   1380
ggtgctacat ccattttagg tgggattcga gacgctgtag ctgatgcagg agggtccgta   1440
gaatttgatg tagcgggtca gtataaaaca aaacctgatg tagctattgt tgttttttggc  1500 gaagaacctt atgctgagtt tcgtggagat gtggagacac tggaatatca accagatcaa   1560
aaacaagatc ttaccctact caagaaactg aaagatcagg gaatacctgt tgttgctgtt   1620
ttcctttctg gacgaccgat gtgggttaat cctgaactta atgccagcga tgctttcgtt   1680
gcagcatggc ttcctggcac agaaggtggc ggtgtggcgg atgtattgtt tacagacaaa   1740
gcgggaaaag tacaacatga tttttgcagga aaattgtcat atagttggcc gcgtacggca   1800
gcccagacaa cagttaaccg tggtgatgca gattataatc cgttatttgc gtatggttac   1860
ggtttaacgt acaaagataa atcgaaagtg ggcactctac ctgaagaaag tggagtaccg   1920
gctgaagcgc gacagaattg a                                             1941
```

<210> SEQ ID NO 8
<211> LENGTH: 647
<212> TYPE: PRT
<213> ORGANISM: Artificial
<220> FEATURE:
<223> OTHER INFORMATION: Synthetic polypeptide

<400> SEQUENCE: 8

```
Cys Ser Ala Ala Ile Ala Gln Glu Gly Ala Ala Pro Ala Ala Met Leu
1               5                   10                  15

His Pro Glu Lys Trp Pro Arg Pro Ala Thr Gln Arg Leu Ile Asp Pro
            20                  25                  30

Ala Val Glu Lys Arg Val Asp Ala Leu Leu Lys Gln Leu Ser Val Glu
        35                  40                  45

Glu Lys Val Gly Gln Val Ile Gln Gly Asp Ile Gly Thr Ile Thr Pro
    50                  55                  60

Glu Asp Leu Arg Lys Tyr Pro Leu Gly Ser Ile Leu Ala Gly Gly Asp
65                  70                  75                  80

Ser Gly Pro Asn Gly Asp Asp Arg Ala Pro Pro Lys Glu Trp Leu Asp
                85                  90                  95

Leu Ala Asp Ala Phe Tyr Arg Val Ser Leu Glu Lys Arg Pro Gly His
            100                 105                 110

Thr Pro Ile Pro Val Leu Phe Gly Ile Asp Ala Val His Gly His Gly
        115                 120                 125

Asn Ile Gly Ser Ala Thr Ile Phe Pro His Asn Ile Ala Leu Gly Met
    130                 135                 140

Thr Arg Asp Pro Glu Leu Leu Arg Arg Ile Gly Glu Val Thr Ala Glu
145                 150                 155                 160

Glu Met Ala Ala Thr Gly Ile Asp Trp Thr Phe Ala Pro Ala Leu Ser
                165                 170                 175

Val Val Arg Asp Asp Arg Trp Gly Arg Thr Tyr Glu Gly Phe Ser Glu
            180                 185                 190

Asp Pro Glu Ile Val Ala Ser Tyr Ser Ala Ala Ile Val Glu Gly Val
        195                 200                 205

Gln Gly Lys Tyr Gly Ser Lys Asp Phe Met Ala Pro Gly Arg Ala Val
    210                 215                 220

Ala Cys Ala Lys His Phe Leu Ala Asp Gly Gly Thr Asp Gln Gly Arg
225                 230                 235                 240
```

```
Asp Gln Gly Asp Ala Arg Ile Ser Glu Asp Glu Leu Ile Arg Ile His
            245                 250                 255
Asn Ala Gly Tyr Pro Pro Ala Ile Asp Ala Gly Val Leu Thr Val Met
            260                 265                 270
Ala Ser Phe Ser Ser Trp Gln Gly Ile Lys His His Gly His Lys Gln
            275                 280                 285
Leu Leu Thr Asp Val Leu Lys Gly Gln Met Gly Phe Asn Gly Phe Ile
            290                 295                 300
Val Gly Asp Trp Asn Ala His Asp Gln Val Pro Gly Cys Thr Lys Phe
305                 310                 315                 320
Asn Cys Pro Thr Ser Leu Ile Ala Gly Leu Asp Met Tyr Met Ala Ala
            325                 330                 335
Asp Ser Trp Lys Gln Leu Tyr Glu Asn Thr Leu Ala Gln Val Lys Asp
            340                 345                 350
Gly Thr Ile Pro Met Ala Arg Leu Asp Asp Ala Val Arg Arg Ile Leu
            355                 360                 365
Arg Val Lys Val Leu Ala Gly Leu Phe Glu Lys Pro Ala Pro Lys Asp
            370                 375                 380
Arg Pro Gly Leu Pro Gly Leu Glu Thr Leu Gly Ser Pro Glu His Arg
385                 390                 395                 400
Ala Val Gly Arg Glu Ala Val Arg Lys Ser Leu Val Leu Leu Lys Asn
            405                 410                 415
Asp Lys Gly Thr Leu Pro Leu Ser Pro Lys Ala Arg Val Leu Val Ala
            420                 425                 430
Gly Asp Gly Ala Asp Asn Ile Gly Lys Gln Ser Gly Gly Trp Thr Ile
            435                 440                 445
Ser Trp Gln Gly Thr Gly Asn Arg Asn Asp Glu Phe Pro Gly Ala Thr
450                 455                 460
Ser Ile Leu Gly Gly Ile Arg Asp Ala Val Ala Asp Ala Gly Gly Ser
465                 470                 475                 480
Val Glu Phe Asp Val Ala Gly Gln Tyr Lys Thr Lys Pro Asp Val Ala
            485                 490                 495
Ile Val Val Phe Gly Glu Glu Pro Tyr Ala Glu Phe Arg Gly Asp Val
            500                 505                 510
Glu Thr Leu Glu Tyr Gln Pro Asp Gln Lys Gln Asp Leu Thr Leu Leu
            515                 520                 525
Lys Lys Leu Lys Asp Gln Gly Ile Pro Val Val Ala Val Phe Leu Ser
            530                 535                 540
Gly Arg Pro Met Trp Val Asn Pro Glu Leu Asn Ala Ser Asp Ala Phe
545                 550                 555                 560
Val Ala Ala Trp Leu Pro Gly Thr Glu Gly Gly Val Ala Asp Val
            565                 570                 575
Leu Phe Thr Asp Lys Ala Gly Lys Val Gln His Asp Phe Ala Gly Lys
            580                 585                 590
Leu Ser Tyr Ser Trp Pro Arg Thr Ala Ala Gln Thr Thr Val Asn Arg
            595                 600                 605
Gly Asp Ala Asp Tyr Asn Pro Leu Phe Ala Tyr Gly Tyr Gly Leu Thr
            610                 615                 620
Tyr Lys Asp Lys Ser Lys Val Gly Thr Leu Pro Glu Glu Ser Gly Val
625                 630                 635                 640
Pro Ala Glu Ala Arg Gln Asn
            645
```

<210> SEQ ID NO 9
<211> LENGTH: 1941
<212> TYPE: DNA
<213> ORGANISM: Artificial
<220> FEATURE:
<223> OTHER INFORMATION: Synthetic DNA construct

<400> SEQUENCE: 9

| | | | | | |
|---|---|---|---|---|---|
| agtgcggcaa | tcacacagga | aggagcagct | ccggccgcta | tgttacatcc | agagaaatgg | 60 |
| cctcgacctg | cgacacaacg | acttattgac | ccggcagttg | aaaaaagagt | tgatgctctg | 120 |
| ttaaaacagt | tatctgttga | agaaaaagta | gggcaagtta | tacagggtga | tattgggaca | 180 |
| attacaccag | aagacctgcg | caaatatcca | ctaggttcta | ttttagccgg | aggagatagc | 240 |
| ggcccgaatg | gagatgatcg | tgctcctcca | aaggagtggc | ttgatctagc | tgatgctttt | 300 |
| taccgtgtaa | gtttagaaaa | acggccaggc | cataccccga | taccagtgct | ttttggcatt | 360 |
| gatgcagttc | atggacataa | caatatcggg | tctgcgacaa | ttttccctca | caatattgca | 420 |
| cttggaatga | cccgtgatcc | agaacttcta | cgaagaattg | gtgaggtaac | agctgaagaa | 480 |
| atggctgcca | cgggaattga | ttggacattt | gcgcctgcac | tgtctgttgt | gagagatgat | 540 |
| cgatggggac | gaacgtatga | aggcttctca | gaagatccag | aaattgtagc | ttcttattca | 600 |
| gcagcaattg | tggaaggctt | tcagggtaaa | tatggttcta | aggatttat | ggcgccgggt | 660 |
| cgcgcggtag | cgtgcgcaaa | gcacttctta | gctgatggtg | aacagatca | aggacgcgat | 720 |
| cagggagatg | cacgcatttc | agaagacgaa | ctaattcgca | ttcataatgc | tggataccct | 780 |
| cctgcgattg | acgcaggagt | gctgacagta | atggcttctt | tttcatcctg | gcaggggatt | 840 |
| aaacaccatg | gccataaaca | acttttaaca | gatgtattaa | aaggacaaat | gggggtttaat | 900 |
| ggatttattg | tgggggattg | gaatgctcat | gaccaagtac | cggctgtac | taaatttaat | 960 |
| tgtccaacat | ctcttattgc | gggtttagat | atgtatatgg | ccgccgattc | ctggaagcag | 1020 |
| ctgtacgaaa | acaccttagc | acaagtgaaa | gatggtacta | ttcctatggc | acgtctagat | 1080 |
| gatgccgtaa | gacgaatctt | gcgagtcaag | gtgttggctg | gcttattcga | gaaacctgcg | 1140 |
| ccaaaagatc | gtccggggtt | accaggcctt | gaaacactag | gatcacctga | acatagagcc | 1200 |
| gtaggccgtg | aagctgttcg | aaaaagccta | gttcttctta | aaaatgataa | aggtaccctt | 1260 |
| ccactgtcac | caaaggctag | agtattagtt | gcaggtgacg | gagcagataa | tattggcaaa | 1320 |
| cagtcggggg | gctggacgat | tagttggcaa | ggaactggaa | accgtaacga | tgaatttccg | 1380 |
| ggtgctacat | ccattttagg | tgggattcga | gacgctgtag | ctgatgcagg | agggtccgta | 1440 |
| gaatttgatg | tagcgggtca | gtataaaaca | aaacctgatg | tagctattgt | tgttttggc | 1500 |
| gaagaacctt | atgctgagtt | tcgtggagat | gtggagacac | tggaatatca | accagatcaa | 1560 |
| aaacaagatc | ttaccctact | caagaaactg | aaagatcagg | gaatacctgt | tgttgctgtt | 1620 |
| ttcctttctg | gacgaccgat | gtgggttaat | cctgaactta | atgccagcga | tgctttcgtt | 1680 |
| gcagcatggc | ttcctggcac | agaaggtggc | ggtgtggcgg | atgtattgtt | tacagacaaa | 1740 |
| gcgggaaaag | tacaacatga | ttttgcagga | aaattgtcat | atagttggcc | gcgtacggca | 1800 |
| gcccagacaa | cagttaaccg | tggtgatgca | gattataatc | cgttatttgc | gtatggttac | 1860 |
| ggtttaacgt | acaaagataa | atcgaaagtg | ggcactctac | tgaagaaag | tggagtaccg | 1920 |
| gctgaagcgc | gacagaattg | a | | | | 1941 |

<210> SEQ ID NO 10
<211> LENGTH: 646
<212> TYPE: PRT

<213> ORGANISM: Artificial
<220> FEATURE:
<223> OTHER INFORMATION: Synthetic polypeptide

<400> SEQUENCE: 10

```
Ser Ala Ala Ile Thr Gln Glu Gly Ala Ala Pro Ala Met Leu His
1               5                   10                  15

Pro Glu Lys Trp Pro Arg Pro Ala Thr Gln Arg Leu Ile Asp Pro Ala
            20                  25                  30

Val Glu Lys Arg Val Asp Ala Leu Leu Lys Gln Leu Ser Val Glu Glu
            35                  40                  45

Lys Val Gly Gln Val Ile Gln Gly Asp Ile Gly Thr Ile Thr Pro Glu
50                      55                  60

Asp Leu Arg Lys Tyr Pro Leu Gly Ser Ile Leu Ala Gly Gly Asp Ser
65                  70                  75                  80

Gly Pro Asn Gly Asp Asp Arg Ala Pro Pro Lys Glu Trp Leu Asp Leu
                85                  90                  95

Ala Asp Ala Phe Tyr Arg Val Ser Leu Glu Lys Arg Pro Gly His Thr
            100                 105                 110

Pro Ile Pro Val Leu Phe Gly Ile Asp Ala Val His Gly His Asn Asn
            115                 120                 125

Ile Gly Ser Ala Thr Ile Phe Pro His Asn Ile Ala Leu Gly Met Thr
130                 135                 140

Arg Asp Pro Glu Leu Leu Arg Arg Ile Gly Glu Val Thr Ala Glu Glu
145                 150                 155                 160

Met Ala Ala Thr Gly Ile Asp Trp Thr Phe Ala Pro Ala Leu Ser Val
                165                 170                 175

Val Arg Asp Asp Arg Trp Gly Arg Thr Tyr Glu Gly Phe Ser Glu Asp
            180                 185                 190

Pro Glu Ile Val Ala Ser Tyr Ser Ala Ala Ile Val Glu Gly Phe Gln
            195                 200                 205

Gly Lys Tyr Gly Ser Lys Asp Phe Met Ala Pro Gly Arg Ala Val Ala
210                 215                 220

Cys Ala Lys His Phe Leu Ala Asp Gly Gly Thr Asp Gln Gly Arg Asp
225                 230                 235                 240

Gln Gly Asp Ala Arg Ile Ser Glu Asp Glu Leu Ile Arg Ile His Asn
                245                 250                 255

Ala Gly Tyr Pro Pro Ala Ile Asp Ala Gly Val Leu Thr Val Met Ala
            260                 265                 270

Ser Phe Ser Ser Trp Gln Gly Ile Lys His His Gly His Lys Gln Leu
            275                 280                 285

Leu Thr Asp Val Leu Lys Gly Gln Met Gly Phe Asn Gly Phe Ile Val
290                 295                 300

Gly Asp Trp Asn Ala His Asp Gln Val Pro Gly Cys Thr Lys Phe Asn
305                 310                 315                 320

Cys Pro Thr Ser Leu Ile Ala Gly Leu Asp Met Tyr Met Ala Ala Asp
                325                 330                 335

Ser Trp Lys Gln Leu Tyr Glu Asn Thr Leu Ala Gln Val Lys Asp Gly
            340                 345                 350

Thr Ile Pro Met Ala Arg Leu Asp Asp Ala Val Arg Arg Ile Leu Arg
            355                 360                 365

Val Lys Val Leu Ala Gly Leu Phe Glu Lys Pro Ala Pro Lys Asp Arg
370                 375                 380

Pro Gly Leu Pro Gly Leu Glu Thr Leu Gly Ser Pro Glu His Arg Ala
```

-continued

```
                385                 390                 395                 400
      Val Gly Arg Glu Ala Val Arg Lys Ser Leu Val Leu Leu Lys Asn Asp
                          405                 410                 415

Lys Gly Thr Leu Pro Leu Ser Pro Lys Ala Arg Val Leu Val Ala Gly
                          420                 425                 430

Asp Gly Ala Asp Asn Ile Gly Lys Gln Ser Gly Gly Trp Thr Ile Ser
                          435                 440                 445

Trp Gln Gly Thr Gly Asn Arg Asn Asp Glu Phe Pro Gly Ala Thr Ser
                  450                 455                 460

Ile Leu Gly Gly Ile Arg Asp Ala Val Ala Asp Ala Gly Gly Ser Val
      465                 470                 475                 480

Glu Phe Asp Val Ala Gly Gln Tyr Lys Thr Lys Pro Asp Val Ala Ile
                          485                 490                 495

Val Val Phe Gly Glu Glu Pro Tyr Ala Glu Phe Arg Gly Asp Val Glu
                          500                 505                 510

Thr Leu Glu Tyr Gln Pro Asp Gln Lys Gln Asp Leu Thr Leu Leu Lys
                          515                 520                 525

Lys Leu Lys Asp Gln Gly Ile Pro Val Val Ala Val Phe Leu Ser Gly
                  530                 535                 540

Arg Pro Met Trp Val Asn Pro Glu Leu Asn Ala Ser Asp Ala Phe Val
      545                 550                 555                 560

Ala Ala Trp Leu Pro Gly Thr Glu Gly Gly Gly Val Ala Asp Val Leu
                          565                 570                 575

Phe Thr Asp Lys Ala Gly Lys Val Gln His Asp Phe Ala Gly Lys Leu
                          580                 585                 590

Ser Tyr Ser Trp Pro Arg Thr Ala Ala Gln Thr Thr Val Asn Arg Gly
                  595                 600                 605

Asp Ala Asp Tyr Asn Pro Leu Phe Ala Tyr Gly Tyr Gly Leu Thr Tyr
                  610                 615                 620

Lys Asp Lys Ser Lys Val Gly Thr Leu Pro Glu Glu Ser Gly Val Pro
      625                 630                 635                 640

Ala Glu Ala Arg Gln Asn
                  645
```